US008868175B2

(12) United States Patent
Arad (Abboud)

(10) Patent No.: US 8,868,175 B2
(45) Date of Patent: *Oct. 21, 2014

(54) APPARATUS AND METHOD FOR ESTIMATING STROKE VOLUME OF THE HEART USING BIO-IMPEDANCE TECHNIQUES

(71) Applicant: Tel Aviv University Future Technology Development L.P., Tel-Aviv (IL)

(72) Inventor: Shimon Arad (Abboud), Tel-Aviv (IL)

(73) Assignee: Tel Aviv University Future Technology Development L.P., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/055,915

(22) Filed: Oct. 17, 2013

(65) Prior Publication Data

US 2014/0046205 A1 Feb. 13, 2014

Related U.S. Application Data

(60) Continuation of application No. 13/371,592, filed on Feb. 13, 2012, now Pat. No. 8,694,089, which is a division of application No. 11/023,912, filed on Dec. 27, 2004, now Pat. No. 8,131,354, which is a continuation-in-part of application No. 10/189,161, filed on Jul. 3, 2002, now Pat. No. 7,096,061.

(51) Int. Cl.
| A61B 5/05 | (2006.01) |
| A61B 5/00 | (2006.01) |
| A61B 5/053 | (2006.01) |
| A61B 6/00 | (2006.01) |

(52) U.S. Cl.
CPC ............. *A61B 5/0536* (2013.01); *A61B 5/7289* (2013.01); *A61B 6/541* (2013.01)
USPC ........... 600/547; 600/300; 600/301; 600/425; 600/509; 600/513; 600/526

(58) Field of Classification Search
CPC .... A61B 5/0205; A61B 5/053; A61B 5/0535; A61B 5/0536; A61N 1/36521
See application file for complete search history.

(56) References Cited

U.S. PATENT DOCUMENTS

| 3,750,649 A | 8/1973 | Severinghaus |
| 4,450,527 A | 5/1984 | Sramek |
| 4,774,952 A | 10/1988 | Smits |

(Continued)

FOREIGN PATENT DOCUMENTS

| EP | 0669822 | 9/1995 |
| EP | 0533732 | 12/1995 |

(Continued)

OTHER PUBLICATIONS

Official Action Dated May 12, 2008 From the US Patent and Trademark Office Re.: U.S. Appl. No. 11/225,630.

(Continued)

*Primary Examiner* — Sean Dougherty

(57) ABSTRACT

A method of estimating stroke volume of the heart is described. In this method, the volume of the heart is estimated from electrical impedance data of the chest, at two different phases of the cardiac cycle. The stroke volume is estimated from the difference between the volumes estimated at the two phases.

8 Claims, 9 Drawing Sheets

(56) References Cited

U.S. PATENT DOCUMENTS

| | | | |
|---|---|---|---|
| 4,974,588 | A | 12/1990 | Smits |
| 5,178,154 | A | 1/1993 | Ackmann et al. |
| 5,311,878 | A | 5/1994 | Brown et al. |
| 5,554,103 | A | 9/1996 | Zheng et al. |
| 5,732,710 | A | 3/1998 | Rabinovich et al. |
| 5,746,214 | A | 5/1998 | Brown et al. |
| 5,749,369 | A | 5/1998 | Rabinovich et al. |
| 5,788,643 | A | 8/1998 | Feldman |
| 6,134,472 | A | 10/2000 | Strandberg et al. |
| 6,224,553 | B1 | 5/2001 | Nevo |
| 6,256,368 | B1 | 7/2001 | Hsieh et al. |
| 6,387,671 | B1 | 5/2002 | Rubinsky et al. |
| 6,438,408 | B1 | 8/2002 | Mulligan et al. |
| 6,511,438 | B2 | 1/2003 | Bernstein et al. |
| 6,517,488 | B1 | 2/2003 | Hossack |
| 6,647,289 | B2 | 11/2003 | Prutchi |
| 6,775,566 | B2 | 8/2004 | Nissilä |
| 6,829,503 | B2 | 12/2004 | Alt |
| 7,096,061 | B2 | 8/2006 | Arad |
| 7,184,821 | B2 | 2/2007 | Belalcazar et al. |
| 2002/0115939 | A1 | 8/2002 | Mulligan et al. |
| 2002/0193689 | A1 | 12/2002 | Bernstein et al. |
| 2003/0074029 | A1 | 4/2003 | Deno et al. |
| 2003/0153958 | A1 | 8/2003 | Yamazaki et al. |
| 2003/0216630 | A1 | 11/2003 | Jersey-Willuhn et al. |
| 2003/0220580 | A1 | 11/2003 | Alt |
| 2004/0006279 | A1 | 1/2004 | Arad (Abboud) |
| 2004/0102712 | A1 | 5/2004 | Belalcazar et al. |
| 2004/0116819 | A1 | 6/2004 | Alt |
| 2004/0220637 | A1 | 11/2004 | Zdeblick et al. |
| 2005/0070778 | A1 | 3/2005 | Lackey et al. |
| 2005/0080460 | A1 | 4/2005 | Wang et al. |
| 2005/0107719 | A1 | 5/2005 | Arad (Abbound) |
| 2005/0107834 | A1 | 5/2005 | Freeman et al. |
| 2005/0124908 | A1 | 6/2005 | Belalcazar et al. |
| 2006/0064029 | A1 | 3/2006 | Arad (Abboud) |
| 2012/0150050 | A1 | 6/2012 | Arad (Abboud) |

FOREIGN PATENT DOCUMENTS

| | | |
|---|---|---|
| EP | 1238630 | 9/2002 |
| GB | 2138148 | 10/1984 |
| GB | 2315332 | 1/1998 |
| JP | 05-507864 | 11/1993 |
| JP | 08-502430 | 3/1996 |
| WO | WO 98/33553 | 8/1998 |
| WO | WO 2004/004539 | 1/2004 |
| WO | WO 2007/031951 | 3/2007 |

OTHER PUBLICATIONS

Official Action Dated Jan. 27, 2009 From the US Patent and Trademark Office Re.: U.S. Appl. No. 11/023,912.
Applicant-Initiated Interview Summary Dated Jun. 26, 2013 From the US Patent and Trademark Office Re. U.S. Appl. No. 13/371,592.
Communication Pursuant to Article 94(3) EPC Dated Jul. 1, 2009 From the European Patent Office Re.: Application No. 03735951.0.
International Preliminary Examination Report Dated May 18, 2006 From the International Preliminary Examining Authority Re.: Application No. PCT/IL03/00556.
International Search Report Dated Aug. 2, 2007 From the International Searching Authority Re.: Application No. PCT/IB2006/053263.
International Search Report Dated May 25, 2004 From the International Searching Authority Re.: Application No. PCT/IL03/00556.
Notification of Reasons for Rejection Dated Nov. 9, 2010 From the Japanese Patent Office Re. Application No. 2004-519141 and Its Translation Into English.
Notification of Reasons of Rejection Dated Jul. 13, 2009 From the Japanese Patent Office Re.: Application No. 2004-519141 and Its Translation Into English.
Notification of Reasons of Rejection Dated Feb. 16, 2010 From the Japanese Patent Office Re.: Application No. 2004-519141 and Its Translation Into English.
Official Action Dated Jun. 2, 2009 From the US Patent and Trademark Office Re.: U.S. Appl. No. 11/225,630.
Official Action Dated Dec. 6, 2005 From the US Patent and Trademark Office Re.: U.S. Appl. No. 10/189,161.
Official Action Dated Jul. 13, 2007 From the US Patent and Trademark Office Re.: U.S. Appl. No. 11/023,912.
Official Action Dated Nov. 13, 2012 From the US Patent and Trademark Office Re. U.S. Appl. No. 13/371,592.
Official Action Dated Oct. 13, 2010 From the US Patent and Trademark Office Re.: U.S. Appl. No. 11/023,912.
Charach et al. "Transthoracic Monitoring of the Impedance of the Right Lung in Patients With Cardiogenic Pulmonary Edema", Critical Care Medicine, 29(6): 1137-1144, 2001.
Dehghani et al. "Incorporating a Priori Anatomical Information Into Image Reconstruction in Electrical Impedance Tomography", Physiological Measurement, XP020073872, 20(1): 87-102, Feb. 1, 1999. Abstract.
Dodge et al. "Quantitative Contrast Angiography for Assessment of Ventricular Performance in Heart Disease", Journal of the American College of Cardiology, p. 73-81, 1983. Abstract.
Dong et al. "Derivation From Current Density Distribution to Conductivities Based on the Adjoint Field Theory and Numerical Test With Finite Volume Method", Proceedings of the 2nd Japan-Australia-New Zealand Joint Seminar on Applications on Electromagnetic Phenomena in Electrical and Mechanical Systems, Kanazawa, Japan, XP002515750, p. 89-96, Jan. 24, 2002. Reetrieved From the Internet: <URL:http://www.ysaitoh.k.hosei.ac.jp/labor/ysaitoh/papers/Conference/2003JSAEM_2ndJANS_Derivation_fromCurrent_Density_Distribution_to_Conductivities_based_on_the_Adjoin_Field_Theory_and_Numerical_Test_with_Finite_Volume_Method.pdf>. Introduction: p. 89, Part 3.1: p. 91-92.
Dong et al. "GVSPM for Reconstruction in Electrical Impedance Tomography", IEEE Transactions on Magnetics, 39(3): 1630-1633, 2003.
Edwardson et al. "A Bioelectrical Impedance Analysis Device for Improved Management of Congestive Heart Failure", Computers in Cardiology, 27: 9-12, 2000.
Eyüboglu et al. "In Vivo Imaging of Cardiac Related Impedance Changes", IEEE Engineering in Medicine & Biology Magazine, 8(1): 39-45, 1989.
Fang et al. "Finite Difference, Finite Element and Finite Volume Methods Applied to Two-Point Boundary Value Problems", Journal of Computational and Applied Mathematics, 139: 9-19, 2002.
Glidewell et al. "Anatomically Constrained Electrical Impedance Tomography for Anisotropic Bodies via a Two-Step Approach", IEEE Transactions on Medical Imaging, XP002515752, 14(3): 498-503, Sep. 1995. Abstract, Part I. Introduction, Part II.B Inverse Problem, Part IV. Step One, Part V. Step Two.
Govreen-Segal et al. "Real-Time PC-Based System for Dynamic Beat-to-Beat QT-RR Analysis", Computers and Biomedical Research, 32: 336-354, 1999.
Greenberg et al "Reproducibility of Impedance Cardiography Hemodynamic Measures in Clinically Stable Heart Failure Patients", ICG Reproducibility in Heart Failure, p. 1-7, 2000.
Griffiths "Tissue Spectroscopy With Electrical Impedance Tomography: Computer Simulations", IEEE Transactions on Biomedical Engineering, XP002515753, 42(9): 948-954, Sep. 1995. Part III.B Numerical Model.
Hoetnik et al. "Comparing Spot Electrode Arrangements for Electric Impedance Cardiography", Physiological Measurement, 23: 457-467, 2002. Abstract.
Imhoff et al. "Noninvasive Whole-Body Electrical Bioimpedance Cardiac Output and Invasive Thermodilution Cardiac Output in High-Risk Surgical Patients", Critical Care Medicine, 28(8): 2812-2818, 2000. Abstract.
Jithesh et al. "A Review on Computational EMI Modeling Techniques", Proceedings of INCEMIC, p. 159-166, 2003.
Lee et al. "Three-Dimensional Forward Solver and Its Performance Analysis for Magnetic Resonance Electrical Impedance Tomography (MREIT) Using Recessed Electrodes", Physics in Medicine and Biology, 48: 1971-1986, 2003.
Li "Multifrequente Impedanztomographie zur Darstellung der elektrischen Impedanzverteilung im menschlichen Thorax", Disser-

(56) References Cited

OTHER PUBLICATIONS tation, Institut f?r Biomedizinische Technik, Stuttgart, Deutsche Nationalbibliothek, XP002515749, Feb. 7, 2007. Retrieved From the Internet: <URL:http://deposit.ddb.de/cgi-bin/dokserv?idn=960463143>. Abstract: p. 13-22, Part 2: p. 31-49, Part 3.2: p. 60-63, Part 4.1: p. 87-89, Part 6: p. 135-157, Figs.4.1, 4.2, 6.1, 6.9, 6.10.
Li et al. "The Finite Volume Method and Application in Combinations", Journal of Computational and Applied Mathematics, 106: 21-53, 1999.
Lucquin et al. "Finite Differences in Time and Finite Volumes in Space", Introduction to Scientific Computing, XVII(Sec.7.8): 300-304, 1998.
Matiussi "An Analysis of Finite Volume, Finite Element, and Finite Difference Methods Using Some Concepts From Algebraic Topology", Journal of Computational Physics, 133: 289-309, 1997.
Newell et al. "Assessment of Acute Pulmonary Edema in Dogs by Electrical Impedance Imaging", IEEE Transactions on Biomedical Engineering, 43(2): 133-138, 1996.
Newell et al. "Phasic Three-Dimensional Impedance Imgaging of Cardiac Activity", Physiological Measurement, 23: 203-209, 2002.
Noble et al. "Monitoring Patients With Left Ventricular Failure by Electrical Impedance Tomography", The European Journal of Heart Failure, XP002515754, 1(4): 379-384, Dec. 1999. Abstract.
Noordegraaf et al. "Pulmonary Perfusion Measured by Means of Electrical Impedance Tomography", Physiological Measurement, XP020073840, 19(2): 263-273, May 1, 1998.
Ollikainen et al. "Effects of Local Skull Inhomogeneities on EEG Source Estimation", Medical Engineering & Physics, 21: 143-154, 1999.
Pruis et al. "A Comparison of Different Numerical Methods for Solving the Forward Problem in EEG and MEG", Physiological Measurements, 14: A1-A9, 1993.
Raaijmakers et al. "The Influence of Extravascular Lung Water on Cardiac Output Measurements Using Thoracic Impedance Cardiography", Physiological Measurement, 19: 491-499, 1998. Abstract.
Record et al. "Multifrequency Electrical Impedance Tomography", Clinical Physics and Physiological Measurement, 13(Suppl.A): 67-72, 1992.
Riu et al. "In Vivo Static Imaging for the Real and the Reactive Parts in Electrical Impedance Tomography Using Multifrequency Techniques", IEEE, p. 1706-1707, 1992.
Rosenfeld et al. "Numerical Solution of the Potential Due to Dipole Sources in Volume Conductors With Arbitrary Geometry and Conductivity" IEEE Transactions on Biomedical Engineering, XP002515751, 43(7): 679-689, Jul. 1996.
Scott et al. "Theoretical Model of Electrode Polarization and AC Electroosmotic Fluid Flow in Planar Electrode Arrays", Journal of Colloid and Interface Science, 238: 449-451, 2001.
Shahidi et al. "Impedance Tomography: Computational Analysis Based on Finite Element Models of a Cylinder and a Human Thorax", Annals of Biomedical Engineering, 23: 61-69, 1995.
Subramanyan et al. "Total Body Water in Congestive Heart Failure—A Pre and Post Treatment Study", Journal of the Association of Physicians in India, 28: 257-262, 1980.
Tang et al. "Effects of Incompatible Boundary Information in EIT on the Convergence Behavior of an Iterative Algorithm", IEEE Transactions on Medical Imaging, 21(6): 620-628, Jun. 2002.
Versteeg et al. "Conservation Laws of Fluid Motion and Boundary Conditions", An Introduction to Computational Fluid Dynamics—The Finite Volume Method, Longman Scientific & Technical, Chap. 2: 10-40, 1995. Only Description and Table of Contents, Article Not Available!
Vonk Noordegraaf et al. "Pulmonary Perfusion Measured by Means of Electrical Impedance Tomography", Physiological Measurement, XP020073840, 19(2): 263-273, May 1, 1998. Part 1. Introduction.
Watkins "Orthogonal Matrices and the Least-Squares Problem", Fundamentals of Matrix Computations, Wiley-Interscience, Chap.3: 134-157, 2002.
Zlochiver et al. "Induced-Current Electrical Impedance Tomography: A 2-D Theoretical Simulation", IEEE Transactions on Medical Imagining, 22(12), 1550-1560, 2003.
Zlochiver et al. "Parametric EIT for Monitoring Cardiac Stroke Volume", Physiological Measurement, 27: S139-S146, 2006.
Official Action Dated Jan. 15, 2010 From the US Patent and Trademark Office Re.: U.S. Appl. No. 11/225,630.
Official Action Dated Nov. 16, 2009 From the US Patent and Trademark Office Re.: U.S. Appl. No. 11/023,912.
Official Action Dated Apr. 20, 2010 From the US Patent and Trademark Office Re.: U.S. Appl. No. 11/023,912.
Official Action Dated Jun. 21, 2011 From the US Patent and Trademark Office Re.: U.S. Appl. No. 11/023,912.
Official Action Dated May 21, 2013 From the US Patent and Trademark Office Re. U.S. Appl. No. 13/371,592.
Official Action Dated Mar. 23, 2005 From the US Patent and Trademark Office Re.: U.S. Appl. No. 10/189,161.
Official Action Dated Oct. 24, 2011 From the US Patent and Trademark Office Re.: U.S. Appl. No. 11/023,912.
Official Action Dated Jan. 28, 2009 From the US Patent and Trademark Office Re.: U.S. Appl. No. 11/225,630.
Official Action Dated Aug. 31, 2004 From the US Patent and Trademark Office Re.: U.S. Appl. No. 10/189,161.
Supplementary European Search Report Dated Mar. 4, 2009 From the European Patent Office Re.: Application No. 03735951.0.
Written Opinion Dated Aug. 2, 2007 From the International Searching Authority Re.: Application No. PCT/IB2006/053263.
Written Opinion Dated Apr. 22, 2005 From the International Preliminary Examining Authority Re.: Application No. PCT/IL03/00556.
Abboud et al. "Numerical Calculation of the Potential Distribution Due to Dipole Sources in a Spherical Model of the Head", Computers and Biomedical Research, 27: 441-455, 1994.
Barber "A Review of Image Reconstruction Techniques for Electrical Impedance Tomography", Medical Physics, 16(2): 162-169, 1989.
Belalcazar et al. "Improved Lung Edema Monitoring With coronary Vein Pacing Leads: A Simulation Study", Physiological Measurement, Institute of Physics Publishing, 25(2): 475-487, 2004. § [04.3], [04.5], [04.6], Figs.5, 7, Table 4.

RESPIRATION

RAW ECG DATA    X10⁴

RR SIGNAL    X10⁴

APPARATUS AND METHOD FOR ESTIMATING STROKE VOLUME OF THE HEART USING BIO-IMPEDANCE TECHNIQUES

RELATED APPLICATIONS

This application is a continuation of U.S. patent application Ser. No. 13/371,592 filed on Feb. 13, 2012, which is a division of U.S. patent application Ser. No. 11/023,912 filed on Dec. 27, 2004, now U.S. Pat. No. 8,131,354, which is a continuation-in-part (CIP) of U.S. patent application Ser. No. 10/189,161 filed on Jul. 3, 2002, now U.S. Pat. No. 7,096,061.

The contents of all of the above applications are incorporated by reference as if fully set forth herein.

FIELD OF THE INVENTION

The present invention relates to the field of instrumentation for monitoring and evaluating patients with heart disease, particularly congestive heart failure.

BACKGROUND OF THE INVENTION

Congestive heart failure (CHF) is a condition in which the heart does not adequately maintain circulation of blood. It is characterized by an increase in retained body water, especially extracellular water, often in the lungs (pulmonary edema). A decrease in extracellular fluid in CHF patients typically indicates an improvement in heart performance. Conventional methods of monitoring CHF patients either require expensive equipment and trained personnel (e.g. measuring pulmonary artery and central venous pressure with catheters, measuring blood flow through the mitral annulus and pulmonary veins with doppler echocardiography) or are not very accurate (e.g. monitoring changes in body weight, observing neck vein distension, measuring ankle dimensions). Impedance measurements of the chest, both resistive and reactive (capacitive) impedance, have been shown to correlate with total body water, extracellular body water, and the ratios of these quantities to fat free mass (U.S. Pat. No. 5,788,643). Monitoring trends in these quantities in congestive heart failure patients is a particularly useful way to determine whether medication doses need to be increased or decreased. As stated in U.S. Pat. No. 5,788,643: "Subramanyan, et al. and others have shown that both the resistive and reactive components of the body's impedance to the flow of relatively high frequency (50 kHz) electrical current is sensitive to the amount of fluid retained by a patient with CHF. As the CHF resolves, resistance and reactance both increase as does the [ratio of reactance to resistance]. See Subramanyan, et al., "Total Body Water in Congestive Heart Failure," Jour. Asso. Phys. Ind., Vol. 28, September, 1980, pages 257-262. It would be most desirable to provide a simple way of detecting increases in body water of patients with CHF before hospitalization is necessary and permitting adjustments in medication and/or diet in time to prevent an episode of acute heart failure." The patent describes a figure of merit, calculated from impedance measurements, for deciding when medical intervention may be needed for a CHF patient.

There are several parameters that affect the impedance of the thorax. The impedance of the chest cavity is small compared to changes in the impedance of the skin, and chest cavity impedance changes substantially during the respiratory cardiac cycle, due to the changing volume of air in the lungs, and during the cardiac cycle due to the changing blood perfusion of the lungs. Various techniques are used to separate out the part of the impedance due to excess body water, and to meaningfully compare such impedance measurements taken in the same patient on different days. For example, U.S. Pat. No. 5,749,369, and Charach, G. et al., "Transthoracic Monitoring of the Impedance of the Right Lung in Patients with Cardiogenic Pulmonary Edema," Crit. Care Med. 2001, Vol. 29, No. 6, pages 1137-1144 discuss ways to compensate for drifting skin impedance.

In addition to the techniques used in bulk measurements of impedance, impedance imaging is also useful for separating out the different contributions to the impedance. In impedance imaging, a set of many electrodes (usually 16 or 32) is placed on the body, for example encircling the chest, and the voltage is measured at each electrode, while a known current is applied between different pairs of the electrodes. The resulting data is used to produce a map of the internal impedance of the body, using various mathematical techniques, some of them similar to those used in x-ray tomography. Some image reconstruction techniques are described in a review paper by D. C. Barber, Med. Phys., (1989), Vol. 16, pages 162-169.

The finite element method, finite difference method, and boundary element method are different techniques used to solve differential equations numerically. Solving Poisson's equation to find the potential distribution in the body due to known current sources and impedance distribution, together with boundary conditions, is known as the forward problem. These numerical methods are used in the field of bio-impedance to solve the forward problem. Rosenfeld, M. et al., "Numerical Solution of the Potential Due to Dipole Sources in Volume Conductors With Arbitrary Geometry and Conductivity," IEEE Transactions on Biomedical Engineering, July 1996, Vol. 43, No. 7, pages 679-689 use a different technique, the finite volume method, to solve the forward problem. The finite volume method is also used to solve the forward problem by Guoya Dong et al, "Derivation from current density distribution to conductivities based on the adjoint field theory and numerical test with finite volume method," presented at the $2^{nd}$ Japan, Australia and New Zealand Joint Seminar, 24-25 Jan. 2002, Kanazawa, Japan, on Applications of Electromagnetic Phenomena in Electrical and Mechanical Systems. Finding the impedance distribution with known potential distribution at the surface (measured with surface electrodes, for example), and known current sources (flowing from one surface electrode to another), is called the inverse problem. Some of the inverse problem solvers use the forward problem solver as a step in an iterative solution.

An early paper on impedance imaging by Eyuboglu, B. M. et al., "In Vivo Imaging of Cardiac Related Impedance Changes," March 1989, IEEE Engineering in Medicine and Biology Magazine, Vol. 8, pages 39-45 discusses the use of gating and time-averaging to separate out the contributions of the respiratory and cardiac cycles to the chest impedance and impedance images, including impedance images of pulmonary embolisms. The authors state, "[T]he resistivity of most tissue changes significantly with blood perfusion into the tissue . . . [I]t has been shown that the thoracic resistivity changes during the cardiac cycle can be imaged by ECG-gated EIT [electrical impedance tomography] . . . . The average resistivity of lung tissue increases with the amount of air inspired . . . [by] approximately 300 percent . . . from maximal expiration to maximal inspiration . . . . The resistivity of lung tissue also changes with the perfusion of blood following ventricular systole . . . . This change has been calculated as 3 percent . . . [which] may be as small as the noise level . . . . Therefore, to pick up the cardiac-related resistivity variations within the thorax during normal breathing, the respiratory component and the noise must be eliminated . . . . The respiratory component may be rejected by temporal averaging . . . . Experience has shown that averaging over at least 100 cardiac cycles is needed during shallow breathing to attenuate the respiratory component and to improve S/N ratio. Cardiac gating is required . . . ." Brown and Barber develop numerical methods to reduce noise in U.S. Pat. No. 5,311,878, and they use differences in impedance at different electrical frequencies between 10 kHz and 600 kHz to distinguish between cardiac and respiratory effects in U.S. Pat. No. 5,746,214. Newell, J. C. et al., "Assessment of Acute Pulmonary Edema in Dogs by Eletrical Impedance Imaging," February 1996, IEEE Transactions on Biomedical Engineering, Vol. 43, No. 2, pages 133-138 demonstrate the use of impedance imaging to detect pulmonary edemas in dogs, and discuss the variability in impedance over time and from day to day, which makes it difficult to measure long-term changes.

The disclosures of the patents and the papers listed above are incorporated herein by reference.

SUMMARY OF THE INVENTION

An aspect of some embodiments of the invention concerns the use of an electrocardiograph (ECG) to measure the depth, frequency, and/or timing of the breathing cycle, in order to be able to correct for the effect of breathing on the chest impedance, which would otherwise mask the effects of pulmonary edema and other symptoms of congestive heart failure on the chest impedance. The breathing cycle is correlated with the RR Intervals extracted from ECG data, because breathing modulates the heart's pacemaker located at the sinuatrial node. Breathing depth also affects the amplitude of the raw ECG data, since the higher impedance of the chest when the lungs are expanded reduces the voltage at the ECG electrodes. By tracking changes in the ECG data at a given point in the cardiac cycle, for example the minimum voltage or the maximum voltage between electrodes during each cardiac cycle, the breathing cycle can be monitored. Although the breathing cycle can also be monitored directly, by measuring air flow into and out of the lungs, this requires more patient cooperation than taking ECG data does, and requires extra equipment, so it is easier to monitor breathing by using ECG data. ECG data is usually obtained anyway in impedance imaging, in order to monitor the cardiac cycle, and no extra equipment is needed if the ECG data is used to monitor the breathing cycle at the same time. Optionally, the system is adapted to be used as home monitoring system, with the information transferred to a remote location where a physician views and diagnoses the condition of a patient. The data can be transferred, for example, by a modem over telephone lines, through secure broadband internet lines, or by another means of communication.

An aspect of some embodiments of the invention concerns solving the inverse problem, i.e. calculating an impedance image of the chest from measured voltages between different pairs from a set of electrodes on the surface of the body, using the finite volume method. The finite volume method offers several advantages over the finite element method and boundary element method for solving the inverse problem, but it has not previously been used for solving the inverse problem in impedance imaging.

An aspect of some embodiments of the invention concerns using ECG data, together with impedance imaging, to evaluate the condition of a congestive heart failure patient, for example in order to determine whether to increase or decrease doses of medication. Diuretics, for example, which are prescribed to reduce pulmonary edema and other symptoms of congestive heart failure, may induce cardiac arrhythmia if taken in too high a dose. In determining the optimal dose, patient outcome is likely to be better if treatment is determined by looking at the overall picture, including symptoms of congestive heart failure and symptoms that may indicate incipient arrhythmia, as well as other symptoms that may be seen in ECG data, rather than simply starting or stopping medication based on isolated symptoms. U.S. Pat. No. 5,788,643 describes a figure of merit for deciding when medical intervention is called for in a CHF patient, but this figure of merit is based only on impedance measurements, not on ECG data.

Optionally, the ECG data is also used to measure the breathing cycle to correct the impedance imaging, as described above. Optionally, the electrodes used for the ECG are also used for the impedance imaging.

An aspect of some embodiments of the invention concerns using impedance imaging to measure the stroke volume of the heart. Impedance measurements are optionally made at the time of end-systole and end-diastole, as determined, for example, by an ECG. The impedance measurements are used to make a best fit to the dimensions of the interior of the heart, which has a high conductivity, and hence to estimate the volume of the interior of the heart, at the two phases. The difference in volumes is a good approximation to the stroke volume.

Optionally, the impedance measurements, whether they are used to measure fluid in the lungs, or to measure stroke volume of the heart, or for another purpose, are performed using an automatic system suitable for use in hospitals.

There is thus provided, in accordance with an embodiment of the invention, a method for generating impedance images of the chest, comprising:

acquiring electrical data of the chest;

obtaining electrocardiograph data of a patient;

analyzing the electrocardiograph data to obtain information about breathing parameters at the time the electrical data was acquired; and reconstructing at least one impedance image of the chest from the electrical data and the information about breathing parameters;

wherein the information about breathing parameters reduces the sensitivity of the at least one impedance image to breathing parameters.

Optionally, reconstructing at least one impedance image comprises:

reconstructing at least one preliminary impedance image of the chest from the electrical data; and correcting the at least one preliminary impedance images to form the at least one impedance image, taking into account the breathing parameters.

Optionally, analyzing the electrocardiograph data comprises analyzing changes in RR intervals.

Alternatively or additionally, analyzing the electrocardiograph data comprises analyzing changes in a voltage measured at a same phase in each cardiac cycle.

Alternatively or additionally, analyzing the electrocardiograph data comprises analyzing the average over one or more cardiac cycles of a voltage measured by the electrocardiograph.

In an embodiment of the invention, reconstructing at least one preliminary image comprises reconstructing a plurality of preliminary images, and correcting the at least one impedance images comprises sorting the preliminary images into a plurality of bins according to the breathing parameters.

Optionally, sorting the preliminary images into bins comprises sorting according to the state of expansion of the lungs.

Alternatively or additionally, sorting the preliminary images into bins comprises sorting according to the elapsed time since the last maximum expansion of the lungs.

Alternatively or additionally, sorting the preliminary images into bins comprises sorting according to the elapsed time since the last minimum expansion of the lungs.

Optionally, sorting the preliminary images into bins comprises sorting according to a cardiac volume.

Alternatively or additionally, sorting the preliminary images into bins comprises sorting according to a heart rate.

Alternatively or additionally, sorting the preliminary images into bins comprises sorting according to a phase of the cardiac cycle.

In an embodiment of the invention, acquiring the electrical data comprises gating by the cardiac cycle.

Optionally, gating by the cardiac cycle comprises using the peak of the R-wave to trigger acquiring the electrical data.

Optionally, correcting the at least one preliminary impedance images comprises averaging the impedance data acquired over one or more breathing cycles.

Alternatively or additionally, reconstructing at least one preliminary image comprises reconstructing a plurality of preliminary images for which the impedance data was acquired at a plurality of phases in the breathing cycle, and correcting the at least one preliminary impedance images comprises averaging the preliminary impedance images.

Optionally, the method includes measuring the air flow into the lungs, and calibrating the information about breathing parameters obtained from the electrocardiograph using said measured air flow.

Alternatively or additionally, the method includes measuring the air flow out of the lungs, and calibrating the information about breathing parameters obtained from the electrocardiograph using said measured air flow.

Optionally, reconstructing at least one preliminary impedance image of the chest comprises using a finite volume method.

There is further provided, according to an embodiment of the invention, a method for generating an impedance image of the chest, comprising:

acquiring electrical data of the chest; and using a finite volume method to calculate an impedance image from the electrical data.

Optionally, the method includes:

formulating an initial impedance image;

using a finite volume method to calculate an expected set of electrical data if the impedance distribution of the chest matched the initial impedance image;

determining a difference between the acquired electrical data and the expected electrical data; and calculating a new impedance image based on said difference.

Optionally, calculating an expected set of electrical data and calculating a new impedance image are iterated at least one time, using the new impedance image calculated in at least one previous iteration to calculate the expected set of electrical data in each iteration except the first iteration.

Optionally, calculating an expected set of electrical data and calculating a new impedance image are iterated until the difference between the acquired electrical data and the expected set of electrical data is small enough to satisfy a stopping condition.

Optionally, calculating the new impedance image comprises calculating with a Newton-Raphson method.

Alternatively or additionally, calculating the new impedance image comprises calculating with a modified Newton-Raphson method.

In an embodiment of the invention, formulating the initial impedance image comprises ascribing typical impedances to different parts of the chest according to at least one image of the chest.

Optionally, ascribing impedances according to at least one image of the chest comprises ascribing impedances according to at least one x-ray image.

Optionally, ascribing impedances according to at least one x-ray image comprises ascribing impedances according to at least one x-ray computed tomography image.

Alternatively or additionally, ascribing impedance according to at least one image of the chest comprises ascribing impedances according to at least one magnetic resonance image.

Alternatively or additionally, ascribing impedances according to at least one image of the chest comprises ascribing impedances according to at least one ultrasound image.

In an embodiment of the invention, using the finite volume method comprises inverting a matrix with a technique that is adapted for inverting sparse matrixes.

Optionally, inverting a matrix comprises inverting a matrix with the successive over relaxation method.

Optionally, acquiring electrical data of the chest comprises measuring potentials at a plurality of locations on the body, while known currents are applied at a plurality of locations on the body.

Optionally, applying known currents comprises applying a current between a first pair of current-applying locations at substantially opposite sides of the chest.

Optionally, measuring potentials comprises measuring the potential difference between two voltage-measuring locations at substantially opposite sides of the chest, different from the first pair of current-applying locations.

Optionally, applying known currents is repeated, using a second pair of current-applying locations that are substantially on opposite sides of the chest and differ from the first pair of current-applying locations.

Optionally, one of the pairs of current-applying locations comprise a location on the left side of the front of the chest and a location on the right side of the back, and the other pair of current-applying locations comprise a location on the right side of the front of the chest and a location on the left side of the back.

There is further provided, in accordance with an embodiment of the invention, a method of estimating stroke volume of the heart, comprising:

generating a first impedance image of the chest according to an embodiment of the invention, at a first phase of the cardiac cycle;

estimating a first volume of the heart from the first impedance image;

generating a second impedance image of the chest according to an embodiment of the invention, at a second phase of the cardiac cycle;

estimating a second volume of the heart from the second impedance image; and using the difference between the first and second volumes of the heart to estimate the stroke volume of the heart.

There is further provided, in accordance with an embodiment of the invention, a method of estimating stroke volume of the heart, comprising:

taking a first set of electrical data of the chest at a first phase of the cardiac cycle;

estimating a first volume of the heart from the first set of electrical data;

taking a second set of electrical data of the chest at a second phase of the cardiac cycle;

estimating a second volume of the heart from the second set of electrical data; and using the difference between the first and second volumes of the heart to estimate the stroke volume of the heart.

Optionally, estimating at least one of the volumes of the heart from the corresponding set of electrical data comprises generating an impedance image of the chest from said set of electrical data.

Optionally, one of the first and second phases of the cardiac cycle comprises an end-systole phase.

Optionally, one of the first and second phases of the cardiac cycle comprises an end-diastole phase.

Optionally, for each of said phases of the cardiac cycle, generating the impedance image comprises generating a two-dimensional impedance image of a slice of the chest, and estimating the volume of the heart comprises estimating a cross-sectional area of the interior of the heart.

Optionally, generating the impedance image comprises modeling the cross-sectional area of the interior of the heart as an ellipse.

Optionally, estimating the volume of the heart comprises modeling the cross-sectional area of the interior of the heart as an ellipse.

Optionally, estimating the volume of the heart comprising using a formula which gives the volume of the heart as a function of the cross-sectional area.

Optionally, the volume is proportional to the square of the cross-sectional area.

Optionally, estimating the first volume of the heart comprises generating a first impedance image of the chest, and estimating the second volume of the heart comprises generating a second impedance image of the chest putting constraints on differences between the second impedance image and the first impedance image, but not constraining the volume of the heart to be the same in the first and second images.

Optionally, the second impedance image, aside from the heart, is constrained to be the same as the first impedance image.

In an embodiment of the invention, acquiring electrical data of the chest comprises measuring potential differences between one or more pairs among a plurality of voltage-measuring locations on the body, while applying known currents at a plurality of current-applying locations on the body.

Optionally, each of the pairs of current-applying locations comprises a location on the left side of the front of the chest, and a location on the right side of the back.

Optionally, for each time the known currents are applied, the plurality of voltage-measuring locations comprises three different locations, at least two of them on the front of the chest, and all three of them different from either of the pair of current-carrying locations at which the known currents are being applied at that time.

There is further provided, in accordance with an embodiment of the invention, a method for monitoring a congestive heart failure patient, comprising:

generating at least one impedance image of the patient's chest;

acquiring electrocardiograph data of the patient; and calculating a parameter characterizing medical treatment of the patient, from electrocardiograph data and at least one impedance image of the chest.

Optionally, calculating at least one parameter comprises calculating a recommended dose of a medication.

Optionally, calculating a recommended dose of medication comprises calculating a recommended dose of a diuretic.

Optionally, using the electrocardiograph data comprises using the QT interval.

Optionally, using the QT interval comprises using the QT interval to detect hypokalemia.

Alternatively or additionally, using the electrocardiograph data comprises using the U wave amplitude.

Optionally, using the U wave amplitude comprises using the U wave amplitude to detect hypokalemia.

There is further provided, in accordance with an embodiment of the invention, an apparatus for making corrected impedance images of the chest, comprising:

an impedance imaging data acquisition system which acquires impedance imaging data of the chest;

an electrocardiograph which obtains electrocardiograph data of a patient; and a data analyzer which analyzes the electrocardiograph data to obtain information about breathing parameters at the time the impedance imaging data was acquired, and reconstructs, from the impedance imaging data and the information about breathing parameters, at least one impedance image of the chest with reduced sensitivity to breathing parameters.

There is further provided, in accordance with an embodiment of the invention, an apparatus for making impedance images of the chest, comprising:

an impedance imaging data acquisition system which acquires impedance imaging data of the chest; and a data analyzer which reconstructs an impedance image of the chest from said impedance imaging data, using a finite volume method.

There is further provided, in accordance with an embodiment of the invention, an apparatus for estimating the stroke volume of the heart, comprising:

an electrocardiograph;

an impedance data acquisition system which acquires impedance data of the chest;

a controller which uses data from the electrocardiograph to trigger the data acquisition system to acquire the data at each of a first phase and a second phase of the cardiac cycle; and a data analyzer which estimates the volume of the heart at the first phase and the second phase from the data acquired at the first phase and the second phase, thereby allowing the stroke volume to be estimated from the difference between the volume of the heart at the first phase and the second phase.

Optionally, the data analyzer is configured to analyze the electrocardiograph data to obtain information about breathing parameters at the time the impedance imaging data was acquired, and is configured to use the information about breathing parameters in estimating the volume of the heart at the first phase and the second phase, thereby making the estimate of the stroke volume more accurate.

Optionally, the electrocardiograph, impedance data acquisition system, and controller comprise a self-contained portable system weighing less than 5 kilograms.

Optionally, there is also a user interface to the controller whereby the user initiates a pre-set sequence of acquisition of the impedance data, the time of the acquisition being triggered by data from the electrocardiograph.

BRIEF DESCRIPTION OF THE DRAWINGS

Exemplary embodiments of the invention are described in the following sections with respect to the drawings. The drawings are generally not to scale. Features found in one embodiment can also be used in other embodiments, even though not all features are shown in all drawings.

DETAILED DESCRIPTION OF EXEMPLARY EMBODIMENTS

Aspects of some embodiments of the invention concern systems for making impedance images of the chest, and for using these images to monitor congestive heart failure patients, or to estimate the stroke volume of the heart. In order to describe the embodiments of the invention shown in FIGS. 2-10, it will be convenient to first describe some prior art shown in FIG. 1. The various options described for FIG. 1 are also options for the embodiments of the invention shown in FIGS. 2-10.

Figure 1:
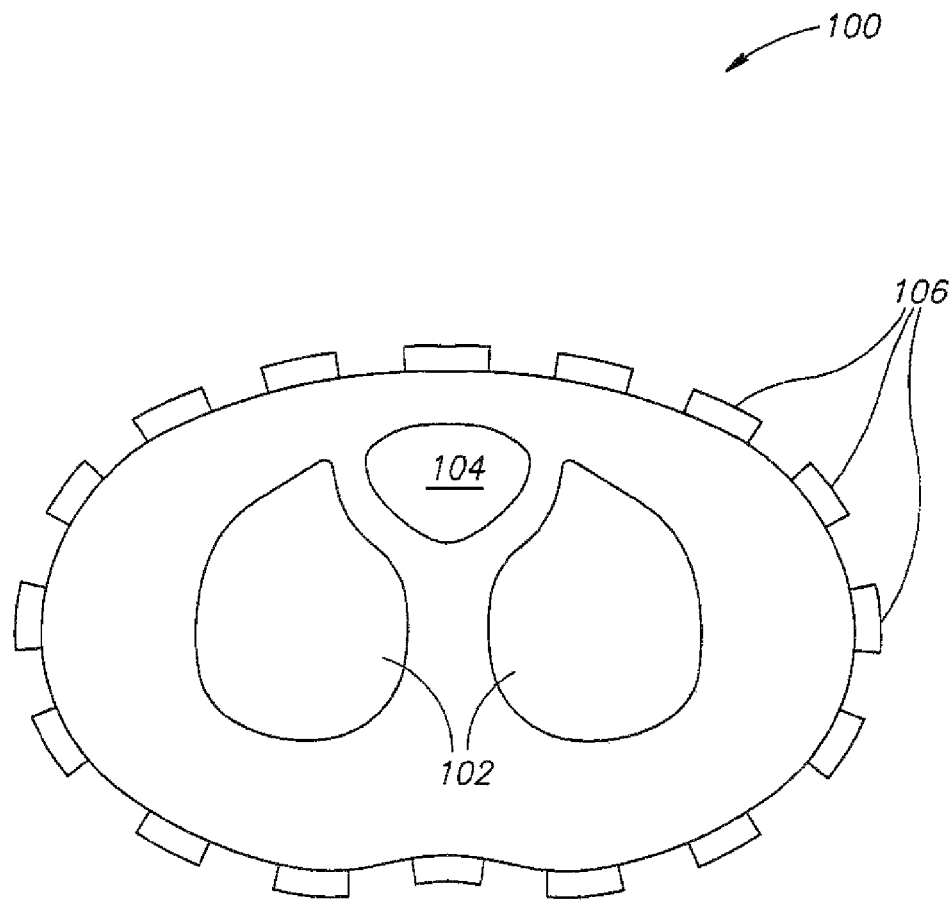
FIG. 1 is schematic view of a cross-section of the chest, showing the placement of electrodes for impedance imaging, according to prior art.

FIG. 1 shows a cross-section of a chest 100, including lungs 102 and a heart 104. An impedance data acquisition system comprises sixteen electrodes 106, shown placed on the skin all around the chest. Although not shown in FIG. 1, the impedance data acquisition system also includes a current source such as a power supply, for passing current through the electrodes, and optionally an amplifier for amplifying voltage measurements made by the electrodes. The number of electrodes used is optionally great enough to obtain a desired resolution in the impedance image, but not so great that the measurements and data analysis take too long. Eight, sixteen and thirty-two are numbers that are commonly used, but other numbers of electrodes may be used. Powers of two have the potential advantage that they are generally more efficient to use for fast fourier transform (FFT) algorithms. To take a set of electrical data for an impedance image, current is first passed through two of the electrodes, and the voltage is measured at all of the electrodes. Then another pair of electrodes is chosen for passing current through, and the process is repeated for many different pairs of electrodes. Optionally, the voltage is not measured on the electrodes with current passing through them, since for those electrodes the voltage tends to be dominated by the voltage drop between the electrode and the skin, so it is difficult to obtain accurate potential measurements on those electrodes. Optionally, more than one pair of electrodes has current passing through it, for one or more of the measurements. In this case, different electrodes optionally have different currents flowing through them. Although this may make the data analysis simpler, it has the disadvantage that there are more electrodes for which it is difficult to get good potential measurements. Optionally, one or more of the electrodes are also used to obtain ECG data.

In FIG. 1, the electrodes are arranged in a single circle around the body, similar to the arrangement used by Eyuboglu, Brown and Barber (loc. cit.). This arrangement may not provide any information about the axial distribution of impedance inside the body, but provides a two-dimensional cross-sectional map of impedance, a weighted average over the axial direction of the three-dimensional impedance distribution. Optionally, the electrodes are arranged not in a single circle, but in two or more circles at different axial positions. Such a two-dimensional grid of electrodes provides data for constructing a three-dimensional map of impedance. More than one circle of electrodes is optionally used for other reasons as well. For example, optionally the positive electrode supplying current is always located in one circle, and the negative electrode with current is always in the other circle. This arrangement provides more independent measurements than if the positive and negative electrodes were chosen from the same circle of electrodes, since in that case switching the two electrodes would not provide any new information. Having one circle of electrodes for potential measurements, and one or two separate circles of electrodes for supplying current, also avoids the problem of measuring potential on an electrode that is supplying current.

Typical currents used for impedance imaging are 1 to 5 milliamps. A current of this magnitude is not dangerous, but is high enough to provide a reasonable signal to noise ratio when measuring the voltage. In order to obtain reactive (capacitive) impedance data as well as resistance data, the currents optionally are AC, typically at frequencies between 10 kHz and several hundred kHz. However, lower frequencies may also be used. For safety reasons, DC current is typically not used in medical procedures, even if reactive impedance data is not needed. Reactive impedance is related to the capacitance of cell membranes, and resistive impedance is related to the volume of water. Because low frequency currents cannot penetrate the cell membranes, low frequency resistive impedance tends to measure only the volume of extracellular water, while high frequency resistive impedance measures the volume of water within cells as well.

Figure 2:
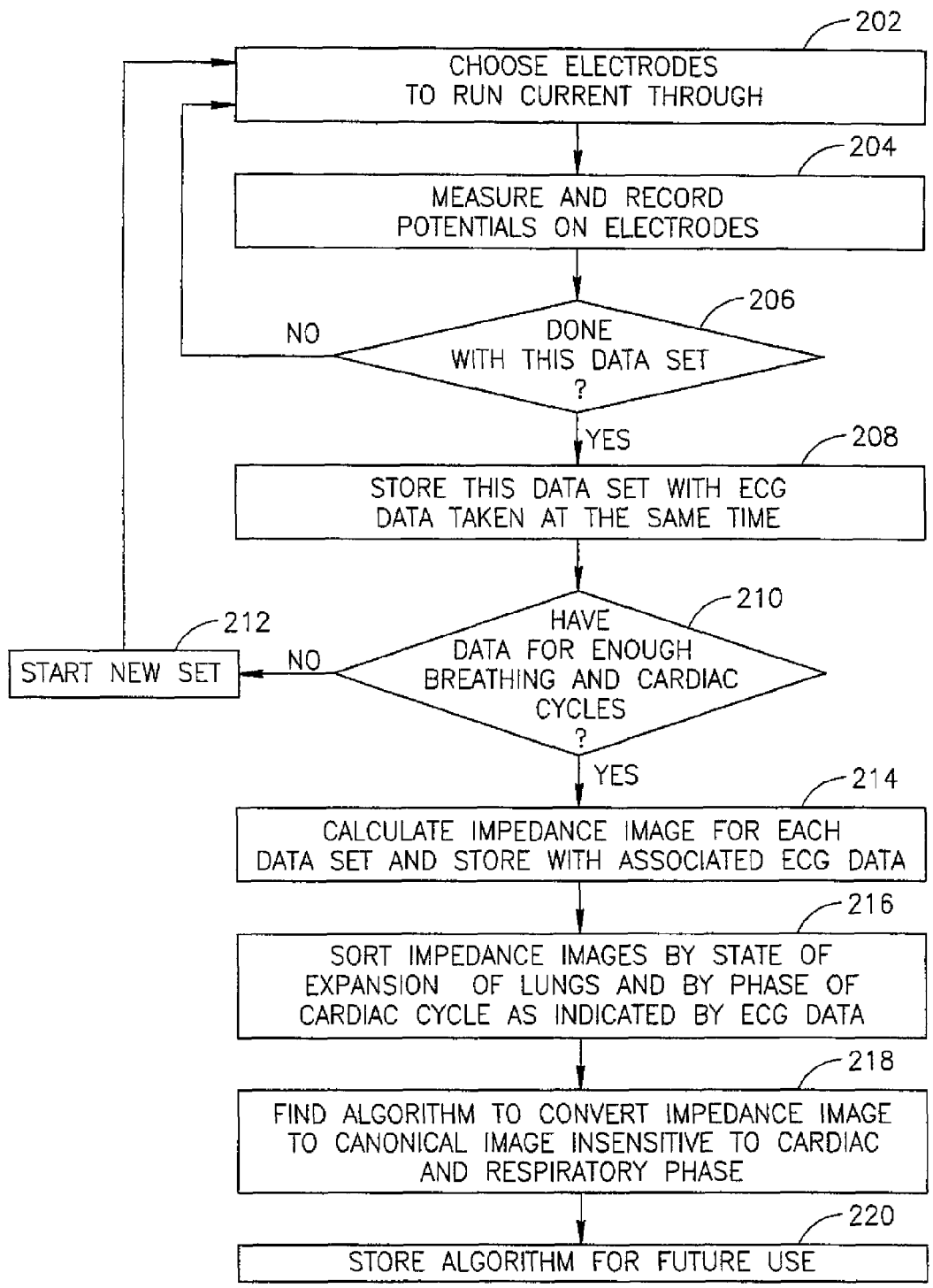
FIG. 2 is a flowchart showing how ECG data is used to distinguish the effect of breathing from the effect of the cardiac cycle on an impedance image of the chest, according to an exemplary embodiment of the invention.

FIG. 2 is a flowchart describing a procedure for using ECG data to monitor the state of expansion of the lungs, and to calibrate impedance images of the chest according to the state of expansion of the lungs. Using this procedure, it may be possible to detect the relatively small changes in impedance associated with changes in thoracic fluid volume, in spite of the larger changes in impedance associated with breathing.

At 202, a pair of electrodes is chosen to apply current. At 204, the voltage is measured and recorded on each electrode, while current is flowing through the chosen electrodes. Optionally, as discussed above, the voltage is not measured on the electrodes carrying current, or certain electrodes are dedicated to carrying current and other electrodes are dedicated to measuring the potential. At 206, the flow goes back to 202 and another pair of electrodes is chosen to carry current, until data has been taken with every possible pair of electrodes, or until it is decided, based on some criterion, that a sufficient set of data has been taken. The potential data is then stored, at 208, together with ECG data taken at the same time. At 210, the procedure goes to 212, and a new set of potential measurements is initiated, until it is decided that a sufficient number of data sets have been taken. Optionally, data sets are taken at intervals short compared to the cardiac cycle time, and data is taken over a period corresponding to several breathing cycles, at least. This allows the impedance images to be correlated with the cardiac and breathing cycles. At 214, after all the data has been taken, an impedance image is computed for each data set, and associated with the ECG data taken at the same time. Optionally, the image is computed using the finite volume method, according to the procedure detailed below in the description of FIG. 4.

At 216, the impedance images are sorted by the phase of the cardiac cycle, and by the state of expansion of the lungs, as indicated by the ECG data taken at the same time the impedance data was measured for that image. The state of expansion of the lungs is optionally inferred from one or both of two different features of the ECG data. When the lungs are in a more expanded state, the RR interval increases, since the expansion of the lungs affects the heart's pacemaker located at the sinuatrial node. Optionally, in using the RR interval to infer the state of expansion of the lungs, variations in the RR interval at frequencies much lower than the breathing frequency are filtered out, since these could be due to other factors which affect the RR interval, for example stress. In addition, the expansion of the lungs increases the resistive impedance of the chest, and this reduces the voltage measured by the ECG electrodes. Normally, in ECG systems, the raw voltage signals are adjusted by pre-amps, which compensate for the slow changes in voltage associated with the breathing cycle, which are not usually of interest. In order to use this aspect of the ECG data to monitor breathing, the pre-amps may be bypassed.

Optionally, the state of expansion of the lungs as inferred from ECG data is calibrated by direct measurements of lung expansion, for example by measuring the air flow into and/or out of the lungs. Optionally, the impedance images are also sorted into bins by the rate of expansion or contraction of the lungs, or other characteristics of the breathing that may affect the impedance image, especially the appearance of pulmonary edemas in the impedance image. If the heartbeat is irregular in strength or timing, then the images are also optionally sorted by systolic volume, interval of ventricular contraction, and other characteristics of the heartbeat that may affect the impedance image.

At 218, the sorted impedance images are converted to a canonical impedance image in which the appearance of pulmonary edema, or the measured thoracic fluid volume, is independent of the cardiac and breathing cycles. At 220, the canonical image is stored. Such a canonical image may be used to meaningfully compare thoracic fluid volume, or other characteristics of a pulmonary edema, at different times, hours or days or weeks apart, and to detect trends which may indicate the need to increase or decrease doses of medication, or to stop or start a given medication, or to intervene medically in other ways.

Optionally, instead of computing preliminary impedance images at 214 and then sorting them at 216, the data sets are sorted at 216, with or without some preliminary processing, and the sorted data sets are used to produce a canonical impedance image at 218. Since the data sets contain the information used to produce the preliminary images, it should be understood that any manipulations performed on the preliminary images to produce a corrected image might instead be performed directly on the data sets without first producing preliminary images.

Several different concepts may optionally be used, singly or in any combination, in processing the images to produce a canonical image:

1. Averaging the images in a given bin (for example, the images taken at a given state of expansion of the lungs, and a given phase of the cardiac cycle), and then taking a linear combination of images in different bins.
2. The coefficients of this linear combination may be negative. For example, if the change in impedance of the lungs associated with a pulmonary edema is correlated with the cardiac cycle, then images taken at one phase in the cardiac cycle may be subtracted from images taken 180 degrees apart in the cardiac cycle. Such a procedure may emphasize pulmonary edemas in the resulting canonical image, and de-emphasize other features of chest impedance that are not of interest.
3. Changes in chest impedance at the breathing frequency, which are likely not to be of interest, are eliminated or reduced by averaging over bins that represent different phases in the breathing cycle, at the same phase in the cardiac cycle.
4. Converting an image taken at any state of lung expansion to an equivalent image at a canonical state of lung expansion, for example with the lungs fully expanded, or the lungs emptied, or half-way in between. An algorithm which does this could make use of a series of impedance images taken at different states of expansion of the lungs.

Optionally, the algorithm for producing a canonical impedance image is adjusted for the particular patient, based on previous data taken for that patient. Additionally or alternatively, the algorithm is based on previous data taken from one or more other patients, possibly from a large number of other patients.

Figure 3A:
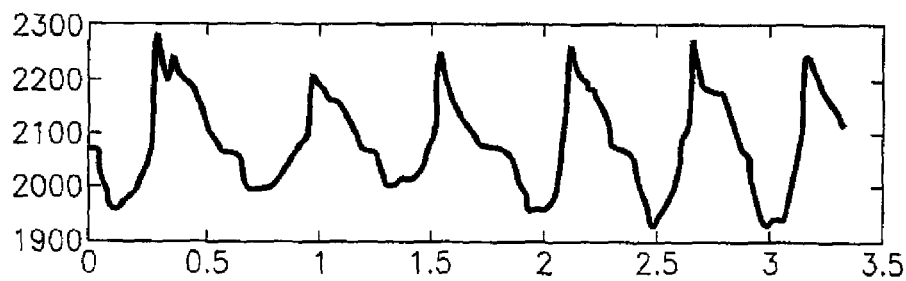
FIGS. 3A, 3B and 3C show breathing data and ECG data, illustrating how the ECG data is affected by breathing.
Figure 3B:
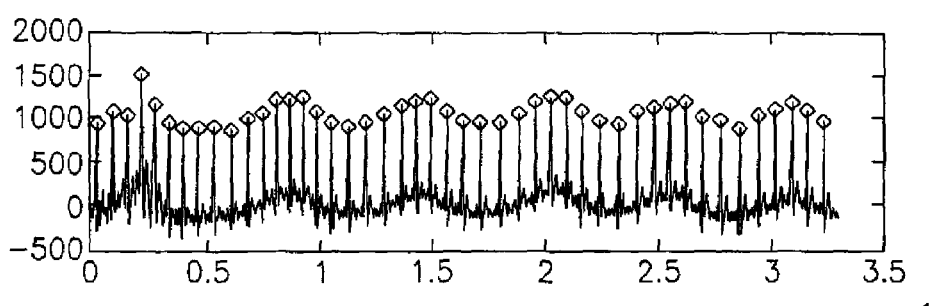
Figure 3C:
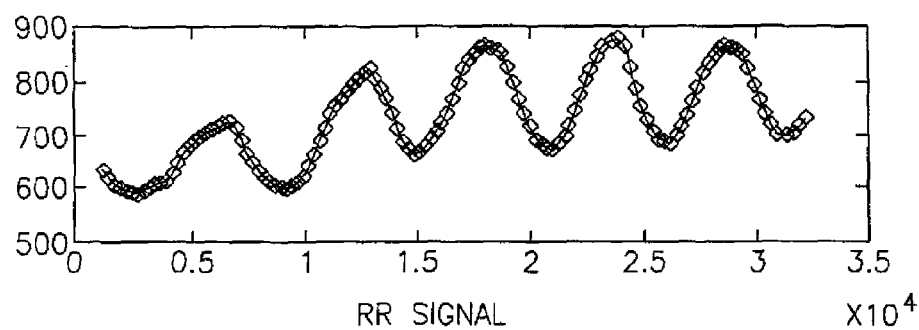

FIG. 3A shows lung volume as a function of time for six breathing cycles, FIG. 3B shows the raw ECG data, and FIG. 3C shows RR interval derived from the ECG data, plotted for the same time period. When the lungs are more expanded, the chest impedance is greater, and the voltage at the ECG electrodes is lower. Hence there is a negative correlation between ECG voltage and lung volume. The RR interval is also correlated negatively with lung volume, because respiration affects the pacemaker of the heart in the sinuatrial node. The correlations between lung volume, raw ECG voltage, and RR interval are strong enough so that ECG voltage and RR interval may be usefully used to monitor the state of expansion of the lungs during breathing.

Figure 4:
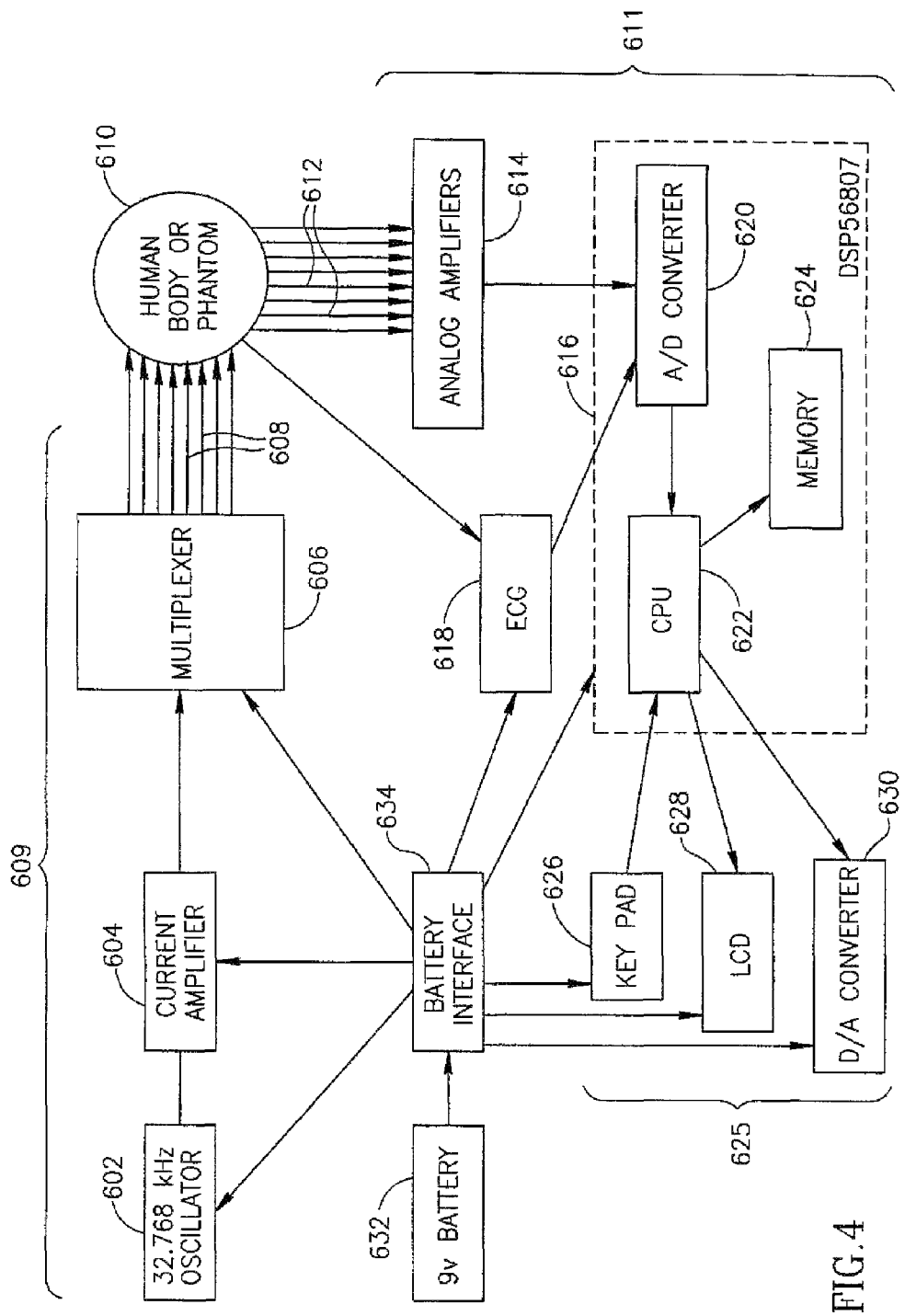
FIG. 4 is a schematic drawing of a hardware configuration for impedance imaging, according to an exemplary embodiment of the invention.

FIG. 4 schematically shows a hardware configuration for an impedance imaging system which uses ECG data to determine breathing parameters, in accordance with an embodiment of the invention. The hardware comprises a current injection module 609, a potential measuring and processing module 611, and a user interface module 625. In the current injection module, a 32.768 kHz oscillator 602 generates a stable sinusoidal current of a few micro-amperes, which is amplified to the desired current, 1 to 5 milliamperes, by current amplifier 604. A dual 1-to-4 multiplexer 606 is used to inject the current through any desired pair chosen from 8 electrodes 608, which are placed around the thorax of a human body 610, or around a phantom. Potential measuring and processing module 611 includes eight electrodes 612, which are applied to the thorax and sense voltage, analog amplifiers 614, and a Motorola DSP56807 chip 616. An electrocardiogram 618 also feeds voltage measurements into chip 616. Chip 616 includes an analog to digital convertor 620 which converts the analog voltage data to digital form, a central processing unit 622, and a memory 624. The digital data is stored in the memory, for each pair of electrodes used to inject current, and is then used by the CPU to reconstruct an impedance image. The CPU also uses the data from the ECG to calculate parameters such as RR and QT intervals, which are used to infer breathing parameters. User interface module 625 includes a keypad 626 used to enter data or feedback from the user into the CPU, a liquid crystal display 628 for presenting the results or for giving instructions to the patient during the measurement process, and a digital to analog convertor 630 for plotting data during development of the system. A 9 volt battery 632 provides power for all three modules, via a battery interface 634, which provides positive and negative voltage and a ground.

Optionally, user interface module 625 is located remotely, with the data transmitted (for example, over phone lines with a modem, or over a secure broadband internet connection), or user interface module 625 includes hardware for transmitting the impedance imaging data from memory 624 to a remote location. Optionally, current amplifier 604 and multiplexer 606 are also controlled remotely, or they are controlled by a computer, optionally chip 616, which is programmed to inject a given sequence of currents through the different electrodes. These options may be useful, for example, for monitoring the condition of a patient who is at home, without the need for him to come into a hospital every time.

Figure 5:
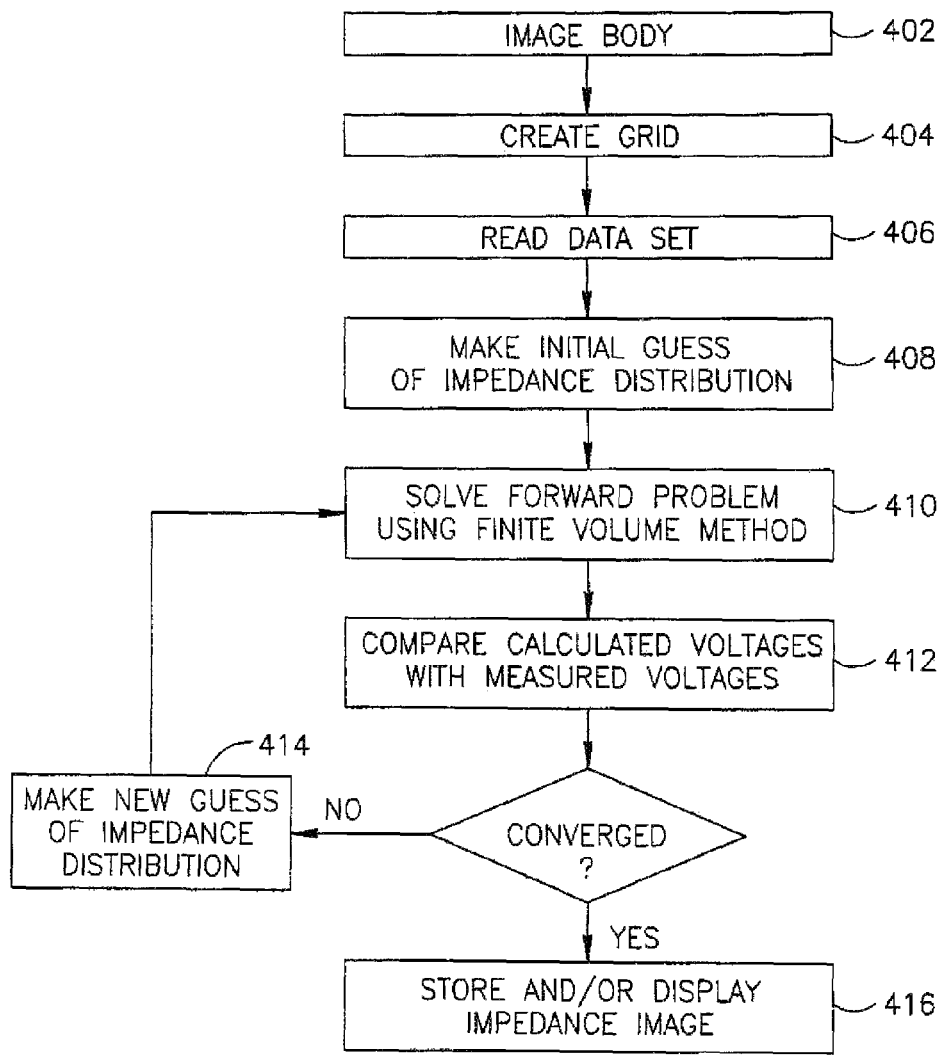
FIG. 5 is a flowchart showing how the finite volume method is used to calculate an impedance image, according to an exemplary embodiment of the invention.

FIG. 5 is a flowchart outlining how the finite volume method is used to calculate an impedance image from the potential data taken with different pairs of electrodes carrying current. Initially, in 402, an image is made of the chest of the patient, using, for example, magnetic resonance imaging, computerized x-ray tomography, or ultrasound. Alternatively, with some loss of accuracy, the patient's chest is modeled by some standard body model, perhaps parameterized by characteristics such as weight, height, gender, and body type. Optionally, the model or image includes the whole body, or more of the body, rather than just the chest, which makes it possible to more accurately account for current paths that are not confined to the chest.

At 404, the chest or body model is used to create a three-dimensional grid. Optionally, the grid conforms to the surface of the body. Optionally, the grid conforms to the surfaces of the lungs and/or the heart, which generally have substantially different impedance from other parts of the chest, and from each other. Optionally, the grid changes during the breathing cycle and heart beat, so that it can continue to conform to the surfaces of the lungs and heart. Alternatively, the grid conforms only to some approximate average surfaces of the lungs and heart, or does not conform to the surfaces of the lungs and heart at all. The grid coordinates of the various electrodes (including their orientations and outlines, as well as their positions) are determined and stored.

In 406, potential data is read at each electrode, for each pair of current-carrying electrodes, as described above in the description of FIG. 1 and FIG. 2. In 408, an initial guess is made of the impedance distribution of the chest, for example, using information about the location of the lungs and heart obtained from the image made in 402, and/or from a chest model used in 402. Optionally, the initial guess for the impedance distribution simply assigns typical values of impedance for lung tissue, cardiac tissue, and the rest of the chest cavity.

In 410, the finite volume method is used to solve the forward problem, calculating the expected surface potential at each electrode where voltage is measured, for each choice of current carrying electrodes, using the initial guess for impedance distribution as a starting point. The finite volume method uses the integral form of Poisson's equation, which becomes a set of simultaneous linear equations when Poisson's equation is discretized and the integral is replaced by a sum. The boundary conditions for Poisson's equation are Neumann-type conditions, stating the current flux normal to the boundary. The finite volume method is more accurate than the finite element method, the most commonly used method in the field of bio-impedance, at solving Poisson's equation with Neumann boundary conditions, because it can treat discontinuous impedance distributions and discontinuous current sources (B. Lucquin and O. Pironneau, *Introduction to Scientific Computing*, John Wiley & Sons, 1998, pp. 300-304), and anisotropic conductivities. Discontinuous impedance distributions are a common feature of the human body, with different body tissues found in well-defined organs, and some body tissues are best modeled by anisotropic conductivities. The finite volume method also makes more efficient use of computational resources and CPU time than the finite element method (Abboud, S. et al, Comput. Biomed. Res., (1994), Vol. 27, pages 441-455). The set of linear equations can be represented in sparse matrix form, and relaxation methods can be used that are very fast and efficient for sparse matrixes, for example the successive over relaxation (SOR) method. The finite volume method also poses less severe restrictions on the quality of the mesh than the finite element method (H. K. Versteeg and W. Malalasekera, An Introduction to Computational Fluid Dynamics—The Finite Volume Method, Longman Scientific & Technical, 1995). The references cited are incorporated herein by reference. In spite of these advantages of the finite volume method, the finite element method has often been used because of the ready availability of commercial forward solvers using the finite element method. The greater speed and more efficient use of computational resources by the finite volume method may be more important when solving the inverse problem than they are when solving the forward problem.

In 412, the surface potential calculated at each electrode in 410, for each chosen pair of current-carrying electrodes, is compared to the voltages measured at each electrode in 406. If the difference between the measured and calculated potentials is small enough, then the initial guess made in 408 for the impedance distribution is a good match to the actual impedance distribution. Otherwise, the Newton-Raphson method or a similar method may be used in 414 to make an improved guess for the impedance distribution, and step 410 (solving the forward problem) is repeated, using the new guess. The Newton-Raphson method involves differentiating (finding the Jacobian of) the matrix associated with the set of linear equations in 410, with respect to changes in the impedance distribution. Here the finite volume method offers another advantage over the finite element method, since the finite volume method allows the matrix elements to be expressed symbolically in terms of the impedance distribution, and the expressions can be mathematically manipulated to find their derivatives, and hence the Jacobian. With the finite element method, on the other hand, the matrix is found only in numerical form, and finding the Jacobian is then much more time consuming, for a large matrix.

The Newton-Raphson method involves inverting a matrix, called the Hessian matrix, which depends on the Jacobian and on the difference between the measured and calculated potentials. Because the Hessian matrix is often ill-conditioned, the Newton-Raphson method may be unstable. Optionally, the stability of the convergence is improved by using a modified Newton-Raphson method, for example the Marquardt method. These methods involve adding to the Hessian matrix a regularization matrix, which makes it better conditioned.

At each iteration of the loop shown in FIG. 5, the calculated potential is compared to the measured voltages on the electrodes. When the difference between them is small enough, the latest guess for the impedance distribution is accepted as a good approximation to the actual impedance distribution. In 416, this impedance distribution is stored, and optionally displayed on a monitor or printed.

Figure 6:
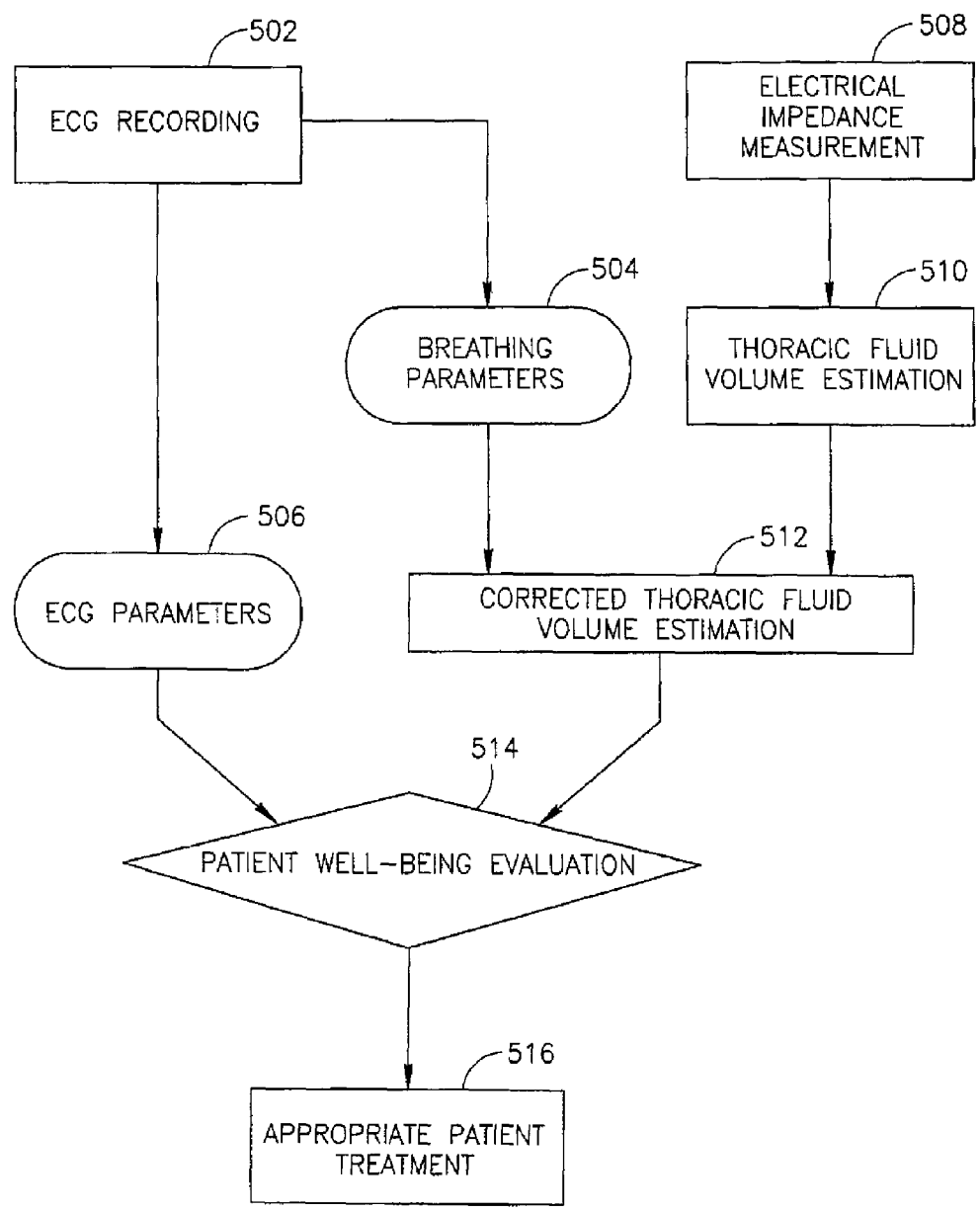
FIG. 6 is a flowchart showing how ECG data and impedance images are used to assess the condition of a congestive heart failure patient, according to an exemplary embodiment of the invention.

FIG. 6 is a flowchart showing how impedance imaging is combined with ECG data to produce an overall evaluation of a patient suffering from congestive heart failure, and to decide on appropriate treatment. ECG data is recorded in 502. This data is used both for determining breathing parameters in 504, as described above in FIG. 2, and for detecting problems with heart function, for example arrhythmia or incipient arrhythmia, in 506. At the same time, in 508, impedance imaging is used to estimate the thoracic fluid volume in 510, and this estimate is adjusted by taking into account the breathing parameters determined in 504. This leads in 512 to a canonical impedance image, as discussed above in FIG. 2, which characterizes the thoracic fluid volume, and the presence of pulmonary edema, independently of the state of expansion of the lungs and the phase of the cardiac cycle at the time the image was made.

In 514, the canonical impedance image in 512 is used, together with the information on cardiac performance in 506, as input to an algorithm which generates an evaluation of the patient's overall condition, with a view toward determining the optimal treatment in 516. For example, an abnormally high thoracic fluid volume by itself might indicate the need for the patient to take an increased dose of diuretic medication. But some diuretics, such as thiazide, furosemide, and ethacrynic acid, can cause or enhance hypokalemia, which if not treated can lead to arrhythmia. If the ECG data in 506 shows abnormally long QT intervals, especially with prominent U waves, then this by itself might indicate hypokalemia and the need to decrease the dose of diuretics. Only by looking at both ECG data in 506 and impedance imaging in 512, is it possible to determine the optimum dose of medication. An algorithm which uses both ECG data and impedance imaging, and finds the optimum treatment, is optionally based, for example, on experience with the outcomes of other patients with similar combinations of symptoms.

Figure 7A:
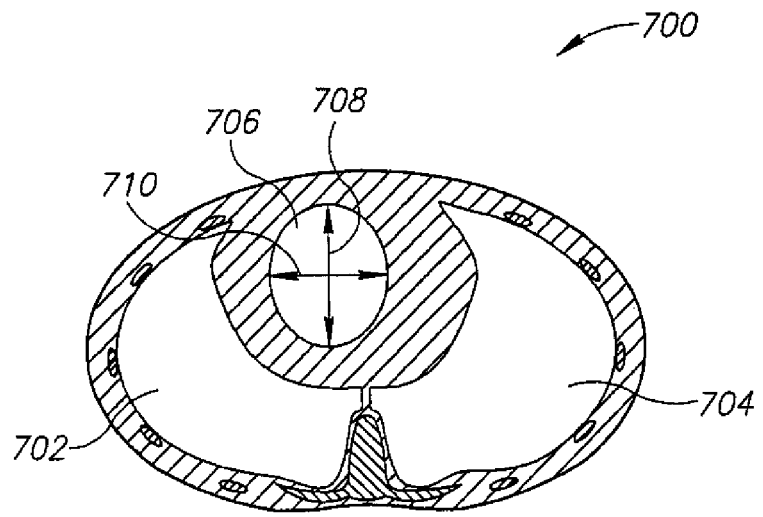
FIGS. 7A and 7B are schematic cross-sectional views of the chest, at end-systole and end-diastole phases respectively, according to an exemplary embodiment of the invention.
Figure 7B:
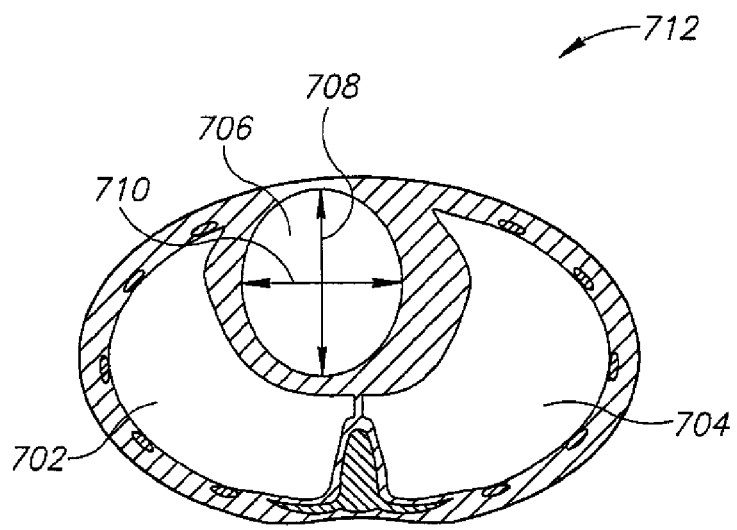

FIGS. 7A and 7B show impedance images of the chest, used to estimate the stroke volume of the heart. The images show a cross-section of the chest, and the impedance data is optionally obtained from electrodes in a belt surrounding the chest, all located approximately in the plane of the cross-section. As discussed above in connection with FIG. 1, impedance data from such electrodes can be used to reconstruct an impedance image in a cross-section of the chest corresponding to the plane where the electrodes are located. Alternatively, the electrodes are distributed at different positions longitudinally, as well as around the chest, and are used to construct a three-dimensional impedance image. Either a two-dimensional or a three-dimensional impedance image may be used to estimate the stroke volume.

FIG. 7A is an impedance image 700 showing the impedance distribution in the cross-section of the chest, at the end-systole phase of the cardiac cycle, when the left ventricle is fully contracted. The impedance image is calculated, for example, using any of the methods described above in the description of the flow chart in FIG. 5, with the impedance measurements gated to the end-systole phase of the cardiac cycle, as indicated, for example, by an ECG. The end-systole phase corresponds to the peak of the R-wave. Optionally, the timing of the end-systole phase is estimated by recording the ECG signal for at least a few cardiac cycles before taking the impedance data, and measuring the RR interval. The impedance data is then taken at the expected time of the next end-systole phase.

The impedance image is optionally made using a low enough frequency, for example 20 kHz, so that it is sensitive mostly to extracellular fluid. (At higher frequencies, for example above 100 kHz, the capacitive impedance of the cell membranes is lower relative to the impedance of the extracellular and intracellular fluid, so much of the current flows through the cells instead of around them. At such high frequencies, the impedance of body tissue is less sensitive to the amount of extracellular fluid, but depends more on the total fluid content.) The lungs 702 and 704, and the interior 706 of the heart, have particularly low impedance.

The interior of the heart, in the plane of the image, is optionally modeled as an ellipse with a principal axis 708 oriented in the anterior-posterior direction, and a principal axis 710 oriented in the left-right direction. The ellipse has diameter "a" in the direction of axis 708, and diameter "b" in the direction of axis 710. Optionally, the center of the ellipse is assumed to be at a particular location which is known to be at least a good approximation to the location of the center of the heart. Alternatively, a best fit to the location of the center of the ellipse is found from the impedance data. This elliptical model is a fairly good approximation to the actual cross-sectional shape of the heart in the plane of electrodes, and using such a model has the potential advantage that a relatively accurate measurement of the heart volume can be made even with only eight electrodes. Alternatively another model is used for the cross-section of the heart, for example it is assumed to be circular, or an ellipse oriented in any direction, or a shape derived from CT images of the heart in the same patient or in an average patient. Alternatively, no assumption is made about the shape of the heart in processing the impedance data to produce an impedance image.

FIG. 7B shows an impedance image 712 of the same cross-section of the chest, derived from impedance measurements gated to the end-diastole phase of the cardiac cycle, when the left ventricle is at its maximum expansion. The end-diastole phase corresponds to, or correlates to, the peak of the T-wave in the ECG, which occurs approximately one third of a cardiac cycle after the end-systole phase. Optionally, the timing of the next end-diastole phase is estimated by measuring the ECG signal for at least a few cardiac cycles, and the impedance measurements are made at the expected time of the next end-diastole phase.

Optionally, the same method is used to calculate impedance image 712 as is used to calculate impedance image 700, optionally including modeling the interior of the heart as an ellipse with principal axes 708 and 710. Optionally, in this case, impedance image 700 is used as an initial guess for calculating impedance image 712. Optionally, in calculating impedance image 712, the impedance distribution is further constrained to be the related in some way to impedance image 700, or to be the same as impedance image 700, except for diameters "a" and "b" of the ellipse, which are allowed to vary to obtain a best fit to the impedance data taken at the end-diastole phase. Alternatively, "a" is constrained to be a particular function of "b," based for example on empirical data showing how the shape of the heart changes as it expands. A potential advantage of using such constraints is that it may be possible to converge more quickly on a relatively accurate measure of the volume of the interior of the heart, and hence on the stroke volume.

Alternatively, the rest of the chest is not assumed to have the same impedance distribution in image 712 as it does in image 700, since the two images may be taken at different phases in the breathing cycle. Optionally the change in the impedance distribution of the rest of the chest during the breathing cycle is modeled, and provides constraints used in calculating impedance image 712. Other methods of dealing with the effects of the breathing cycle are described below.

Alternatively, impedance data for image 712, at the end-diastole phase, is taken first, and impedance image 700, using data taken at the end-systole phase, is calculated by constraining the impedance image to be the same except for the heart diameters "a" and "b," or at least image 712 is used as an initial guess for calculating image 700. A potential advantage of using the end-systole image as an initial guess for the end-diastole image is that the shape and volume of the interior of the heart is likely to be more constant at the end-systole phase than at the end-diastole phase, especially for patients with an irregular heart beat.

Once images 700 and 712 have been found, additional impedance measurements are optionally made at the end-systole and/or at the end-diastole phase, using any of the previous images singly or in combination as initial guesses for calculating additional impedance images. This done, for example, to improve accuracy by averaging over several cardiac cycles and/or several breathing cycles. Optionally, impedance measurements are also made during the expansion and/or during the contraction of the heart, to verify that impedance data for images 700 and 712 really was taken near the end-systole and end-diastole phases. However, such images, made when the volume of the heart is changing, may be less accurate than images 700 and 712.

Optionally, measures are taken to insure that the lung volume is not very different between impedance images 700 and 712, so that it is realistic to treat the two impedance images as identical except for diameters "a" and "b" of the heart. For example, the impedance measurements for images 700 and 712 are gated to be at a same phase in the breathing cycle. or the patient holds his breath while the impedance measurements are made. Alternatively, several sets of impedance measurements are made at different phases in the breathing cycle, and two impedance images are chosen that are from nearly the same phase in the breathing cycle. Alternatively, both impedance images are made using data that is averaged over a breathing cycle. Alternatively, the impedance measurements for image 712 are made at the end-diastole phase immediately following the end-systole phase at the measurements for image 700 are made, close enough in time so that the lung volume hasn't changed very much, possibly choosing a time in the breathing cycle when the lungs are near their maximum or minimum volume.

The area A of the ellipse used to model the cross-sectional area of the interior of the heart is given by $A = \pi ab/4$. The volume V is then estimated by using the formula $$V = 8A^2/(3\pi L)$$

described by H. T. Dodge and F. H. Sheehan, "Quantitative contrast angiography for assessment of ventricular performance in heart disease," *J. Am. Coll. Cardiol.* 1, 73 (1983). The estimated stroke volume is then the change in the volume V between the end-systole phase, using the values of "a" and "b" in image 700, and the end-diastole phase, using the values "a" and "b" in image 712.

Alternatively, if a three-dimensional impedance map is reconstructed, for example from impedance data taken from electrodes that are not all in the same plane, then the effective length of the interior of the heart is optionally estimated from the impedance map, rather than inferred from area A, and the volume V is found by multiplying A by the effective length.

Figure 8:
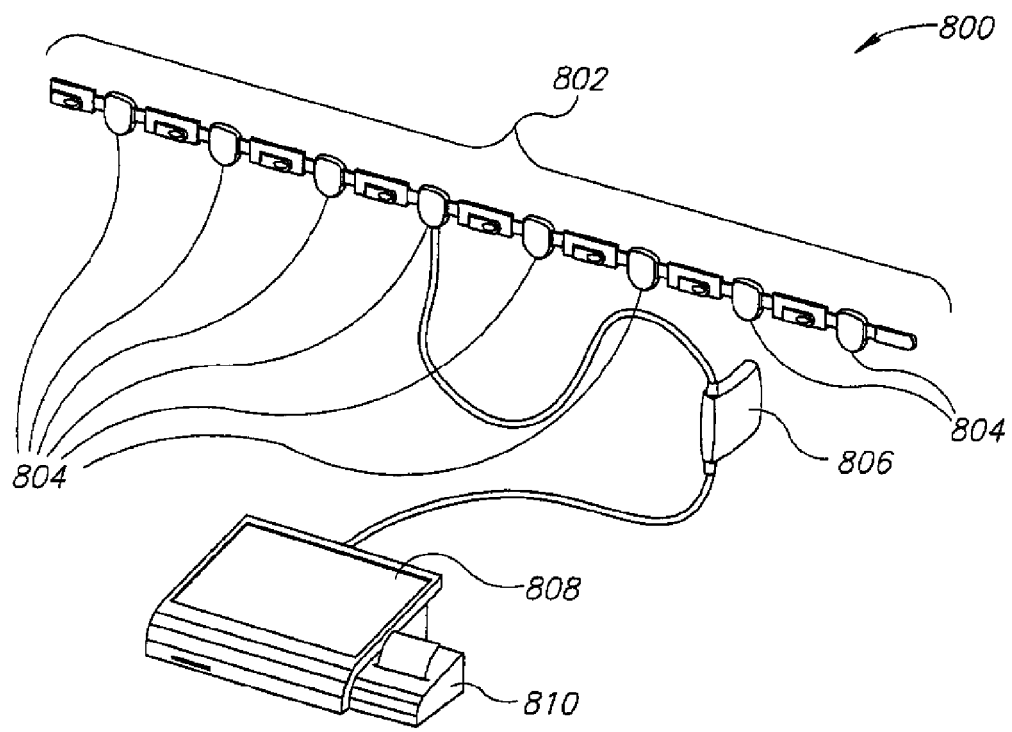
FIG. 8 is a perspective view of a hospital bio-impedance system, according to an exemplary embodiment of the invention.

FIG. 8 shows a bio-impedance system 800, used to obtain impedance images of the chest, to evaluate fluid in the lungs, or stroke volume of the heart, for example, in a non-invasive and relatively rapid way. The unit includes a chest belt 802 with eight electrodes 804. Alternatively a different number of electrodes is used, for example 4, 16 or 32, or another number, even a number that is not a power of 2. Optionally, the electrodes are disposable, and all the electrodes are replaced by new electrodes, inserted into connectors in the belt, for each new patient. Optionally, the chest belt comes in different sizes, appropriate for patients with different chest sizes, and optionally, the length and/or tension of a given size belt is adjustable within limits. Optionally, the electrodes are precisely positioned around the patient's chest, for example at equal distances around the chest, and/or with one or more of the electrodes at a good position for taking ECG data. Alternatively, the electrodes are not precisely positioned, but the positions of the different electrodes optionally are measured and taken into account in reconstructing the impedance images.

An analog amplification unit 806 optionally generates the currents that are passed through the electrodes to measure the impedance, and controls the voltage measurement sequence. As described above for FIG. 1, optionally only some of the electrodes are used to run current through, while other electrodes are used to measure voltage. Optionally, some or all of the electrodes are used sometimes for running current through, and sometimes for measuring voltage, but not at the same time. Alternatively, at least some of the electrodes are used to measure voltage while they have current running through them.

System 800 also includes a base unit 808, which optionally includes a graphical display and a DSP unit. Optionally, some or all of the features shown in the impedance imaging system in FIG. 4 are also found in system 800. Optionally, FIG. 8 illustrates a particular packaging of the system shown in FIG. 4, or another system, that is easily portable and suitable for use in hospitals. For example, system 800 weighs between 2 and 3 kg, or between 3 and 4 kg, or between 4 and 5 kg, or less than 2 kg or more than 5 kg.

System 800, in addition to making impedance measurements, optionally uses at least one of the electrodes in electrode belt 802 to obtain ECG data. The ECG data is optionally processed by a controller, such as a small computer or RISC chip, located in the base unit or in the amplification unit, to determine the phase of the cardiac cycle in real time, so that the impedance measurements can be synchronized to the phases of the cardiac cycle.

Optionally, the ECG data is from a single lead. Optionally, the ECG signal from this electrode is displayed on graphical display in real time, at low resolution, for example 50 pixels per second. Optionally, the operator synchronizes the impedance measurements with the displayed ECG signal manually, for example by pressing a start button on the base unit.

Additionally or alternatively, the system measures the ECG signal, from one or more electrodes, at greater time resolution, in order to accurately trigger the impedance measurement at a phase of the cardiac cycle. For example, the ECG signal is measured at intervals of 1 msec, optionally with 12-bit resolution, and a real time algorithm detects the peak of the R wave, and triggers the impedance measurement automatically. Optionally, as described above for FIGS. 7A and 7B, the peak of the T-wave is also detected or estimated, and used to trigger an impedance measurement, for example for measuring the stroke volume of the heart.

Optionally, the impedance measurement, once it is triggered manually or automatically, is performed by injecting current, for example at 20 kHz, into one or more electrodes. The current is collected at one or more electrodes, while the voltage (both amplitude and phase relative to the current) is measured at the same electrodes and/or at other electrodes that are floating. For example, current is passed successively between each of the 28 possible pairs of two electrodes chosen from the 8 electrodes in the belt, while voltage is measured by the other 6 electrodes which are floating. This set of measurements may provide all of the useful impedance information available from a system with 8 electrodes. The voltage at the electrodes that the current passes through may be dominated by the impedance of the skin, and be insensitive to the impedance of the interior of the chest. Passing current through more than two electrodes may not provide additional information, because it is equivalent to a linear combination of passing current through different pairs of electrodes. Voltage measurements are optionally taken at 200,000 samples per second, at 12 bit resolution, appropriate for making accurate amplitude and phase measurements of a 20 kHz signal.

Figure 9:
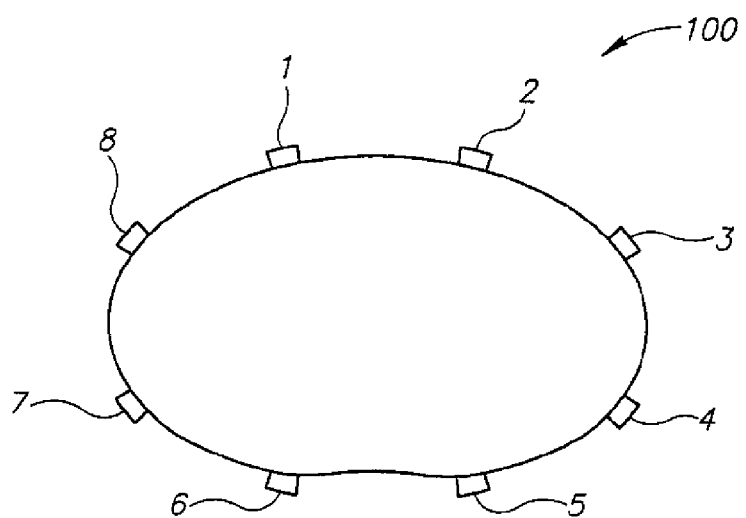
FIG. 9 is a schematic cross-sectional view of the chest, showing the placement of 8 electrodes, using the bio-impedance system shown in FIG. 8.

Alternatively, instead of running current through all possible pairs of electrodes, and measuring voltage at each of the other 6 electrodes in each, current is only run through selected pairs of electrodes, and voltage is only measured between selected pairs of electrodes, which are particularly useful for measuring the impedance of the interior of the chest. For example, FIG. 9 shows the 8 electrodes of the belt, numbered 1 through 8, arranged around a chest 100. Electrodes 1 and 2 are located on the chest, in front, 3 and 4 are located on the right side of the body, electrodes 5 and 6 are located on the back, and electrodes 7 and 8 are located on the left side of the body. Tests have shown that, for measuring fluid in the lungs, it is particularly useful to inject current between electrodes 7 and 3 while measuring voltage between electrodes 8 and 4, and to inject current between electrodes 8 and 4, while measuring voltage between electrodes 7 and 3. For measuring stroke volume of the heart, tests have shown that it is useful to inject current between electrodes 5 and 1 while measuring voltage at electrodes 8 and 3, and between electrodes 8 and 2, and to inject current between electrodes 8 and 4, while measuring voltage between electrodes 1 and 3, and between electrodes 1 and 5. Limiting voltage measurements to these cases produces results for lung fluid and stroke volumes that are almost as good as if all possible measurements were made, while greatly reducing the time needed to take data, and the complexity of the data analysis. Alternatively, different combinations of electrodes are used. Alternatively, a larger set of measurements is made, but still not using all possible combinations of electrodes, for example current is injected through each of three different pairs of electrodes, and two voltage measurements are made for each pair of current-carrying electrodes. Optionally, only the electrodes that are needed for a particular set of measurements are actually present. For example, if only fluid in the lungs is to be measured, using the set of measurements described above for this purpose, then optionally the belt only has four electrodes, corresponding to electrodes 3, 4, 7, and 8 in FIG. 9. Alternatively, instead of spacing these four electrodes as shown in FIG. 9, they are spaced evenly around the chest.

Each measurement preferably lasts for at least several cycles of the AC current, with adequate dead time between measurements, so that accurate amplitude and phase measurements of the voltage can be made. The total time of all the measurements is optionally short compared to a cardiac cycle or a breathing cycle, so that all of the measurements are made at the same phase of the cardiac and breathing cycles. Alternatively or additionally, the measurements are made over more than one cardiac or breathing cycle, but are optionally gated to the cardiac and/or breathing cycles, so that there is enough time to make all the measurements, and/or to improve accuracy by averaging over more than one measurement. Alternatively or additionally, the measurements are made over a range of phases of the cardiac cycle and/or the breathing cycle, but are binned according to the phase of the cardiac cycle and/or the breathing cycle. Alternatively or additionally, measurements are taking over a limited range of phases of the cardiac cycle and/or the breathing cycle, but in a part of the cycle where the heart (in the case of the cardiac cycle) or the lungs (in the case of the breathing cycle) are near a maximum or minimum in volume. Optionally, averaging or other data processing is done in real time while the data is taken.

Optionally, in addition to using the ECG data to trigger the impedance measurements, information obtained from the ECG data, for example the RR interval, the QT interval, and/or the QTc interval, is calculated and displayed on the graphical display, and/or included in a data file of the impedance data. This information from the ECG may be useful, for example, in evaluating the health of the patient, and in interpreting the medical significance of the lung fluid measurements and/or stroke volume measurement obtained from the impedance data.

Optionally, the impedance data is stored, and the impedance images are calculated later. Alternatively, system 800 includes a computer of adequate power to calculate impedance images in real time. Alternatively, a computer or a controller in system 800 does not make full calculations of the impedance image in real time, but analyzes the data sufficiently to verify that the data is reasonable, and is not affected, for example, by inadequate contact between one of the electrodes and the skin, or by a malfunction in the amplification unit, and warns the operator in real time if the data is not good.

Optionally, system 800 has the ability to make a wireless transfer of impedance data, and/or results calculated from the impedance data such as impedance images, for example for archiving purposes. The wireless data transfer capability optionally also allows system 800 to receive data from other devices, for example data about the patient such as weight, that may be used in calculating the impedance images or in evaluating them. The wireless data transfer is done, for example, using an infra-red transceiver or a wireless modem device. In addition to or instead of wireless data transfer capability, system 800 also optionally has data ports such as an R232 interface, for data input and/or output. Optionally, system 800 prints out certain information obtained from the impedance measurements or ECG, either through a data port, or using a printer 810 incorporated in the base unit for example. Optionally, the printer is an inexpensive and/or light weight and/or low power printer, such as a thermal printer.

System 800 is optionally battery operated, which has the potential advantages of low electrical noise and improved safety. Optionally the battery is rechargeable, and optionally system 800 can run for at least 5 hours before recharging or replacing the battery. Optionally, the system has an "idle" mode which reduces power consumption by turning off power consuming elements that are not being used. A low battery indicator is optionally included.

The graphical display optionally has touch screen capability. For example it is a touch screen LCD with a black and white graphical display, with 320 by 240 pixels. Alternatively a different kind of graphical display, or a color display, or a display with a different number or arrangement of pixels is used. Optionally there are no operating buttons for the system except the touch screen.

Figure 10:
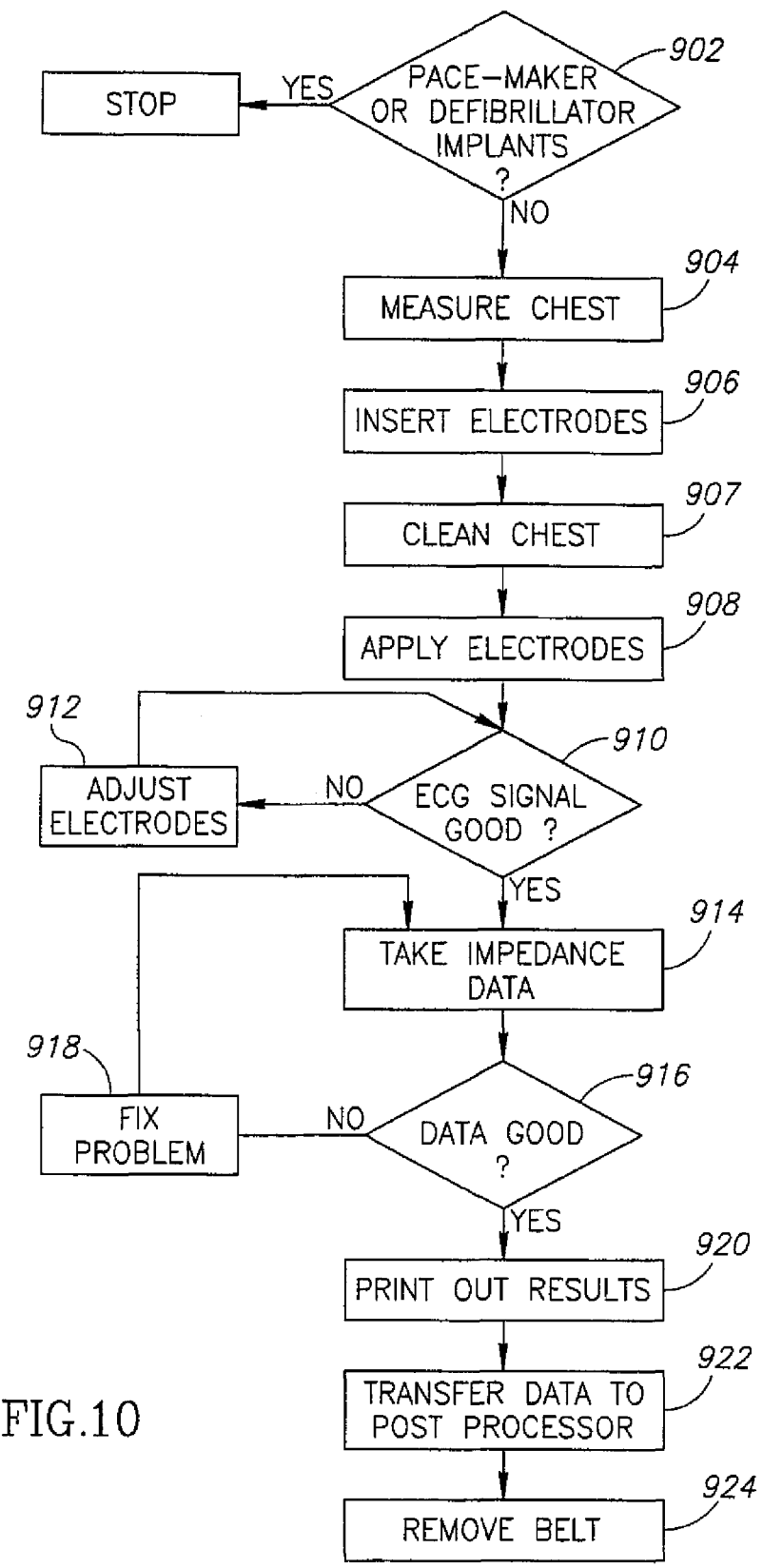
FIG. 10 is a flow chart showing a procedure for using the bio-impedance system shown in FIG. 8.

FIG. 10 is a flow chart showing an exemplary procedure for using system 800. In 902, the operator makes sure that the patient does not have any pace-maker or defibrillator implants, since even the low currents used for the impedance measurements could dangerously affect such implants. If the patient does not have such implants, then the patient's chest is measured, in 904, to determine which size belt to use. In 906, the disposable electrodes are inserted into the proper connectors in the chest belt. In 907, the patient's chest is cleaned, and in 908 the chest belt with the electrodes is applied to the chest. In 910, the ECG signal is monitored, to verify that the electrodes are properly placed, and if not, their positions are adjusted, and/or the tension of the belt is adjusted, in 912, and the ECG signal is monitored again, until the electrodes are properly placed.

In 914, the sequence for taking impedance data is initiated, for example by pressing a start key on the touch screen. The sequence comprises, for example, the six voltage measurements made while sending current through each of the 28 pairs of electrodes, or a useful subset of those measurements, as described above. Optionally, the whole sequence is automated, including triggering by the ECG signal, without the need for any intervention by the operator. Optionally, at least a preliminary analysis is made of the data in 916, and if there is an indication that the data is not good, due for example to a malfunction of the system or improper placement of the electrodes, the system indicates this and optionally diagnoses the problem, for example by a message on the graphical display and/or by an audible tone such as a beep. The operator then optionally attempts to correct the problem in 918, and initiates the data taking sequence again.

When the sequence is successfully completed, as indicated for example by a message on the graphical display, and/or an audible signal, then at least a portion of the results are optionally printed out, in 920, for example by pressing a print key on the touch screen. Alternatively or additionally, some or all of the results are displayed on the graphical display. If some results require post-processing on a computer not included in system 800, then the data needed for the post-processing is transferred to the computer through a data port in 922, either automatically at the end of the data taking sequence, or when requested by the operator, for example by pressing a button on the touch screen. Alternatively, this data transfer is done before printing out the results, or at the same time. The chest belt is removed in 924, the disposable electrodes are removed from the belt, and the patient's chest is cleaned.

The word "data analyzer" as used herein means any equipment used to analyze data, even if it is not a single unit. For example, when a data analyzer is described as analyzing electrocardiograph data and reconstructing an impedance image, this does not necessarily mean that a single piece of equipment does both the analyzing and the reconstructing. The word "data analyzer" can include one or more ordinary computers running software, one or more pieces of specially designed hardware, or both. The words "comprise", "include" and their conjugates as used herein mean "include but are not necessarily limited to". While the invention has been described with reference to certain exemplary embodiments, various modifications will be readily apparent to and may be readily accomplished by persons skilled in the art without departing from the spirit and scope of the above teachings.

What is claimed is:

1. A method of estimating stroke volume of the heart, comprising:
    a) making a first set of electrical measurements of the chest, at a first phase of the cardiac cycle;
    b) estimating a first volume of the heart from data of the first set of electrical measurements;
    c) making a second set of electrical measurements of the chest, at a second phase of the cardiac cycle;
    d) estimating a second volume of the heart from data of the second set of electrical measurements;
    e) finding a difference between the first and second volumes of the heart; and
    f) using the difference between the first and second volumes of the heart to estimate the stroke volume of the heart;
wherein estimating the first volume of the heart comprises generating a first impedance image of the chest from the data of the first set of electrical measurements, and estimating the second volume of the heart comprises generating a second impedance image of the chest from the data of the second set of electrical measurements, and generating the second impedance image of the chest comprises putting constraints on differences between the second impedance image and the first impedance image, but not constraining the volume of the heart to be the same in the first and second impedance images.

2. A method according to claim 1, wherein the first and second impedance images are generated using electrical data obtained using only four, five, six, seven or eight different electrodes, and not using electrical data obtained using additional electrodes.

3. A method according to claim 1, wherein generating the first and second impedance images comprises constraining the images to agree with a model for an interior region of the heart, with at least one or more geometric parameters of the interior region in the first and second images selected to provide a fit respectively to the first and second sets of electrical data.

4. A method according to claim 3, wherein the geometric parameters comprise one or more dimensions of the interior region.

5. A method according to claim 4, wherein the geometric parameters also comprise one or both of an orientation and a position of the interior region.

6. A method according to claim 4, wherein the interior region of the heart is modeled as having an elliptical cross-section, with dimensions along principal axes of the ellipse selected to provide the fit to the electrical data.

7. A method according to claim 1, wherein the first and second impedance images are two-dimensional images of a slice of the chest, and the first and second volumes of the heart are estimated from cross-sectional areas of an interior region of the heart in the first and second images.

8. A method according to claim 1, wherein the electrical data comprises at least one measurement of voltage between a pair of electrodes, while current is passed between other electrodes.

* * * * *